United States Patent
Sundermeyer et al.

(10) Patent No.: US 9,353,139 B2
(45) Date of Patent: May 31, 2016

(54) METAL COMPLEXES WITH N-AMINOAMIDINATE LIGANDS

(75) Inventors: Joerg Sundermeyer, Marburg (DE); Wolf Schorn, Giessen (DE); Ralf Karch, Kleinostheim (DE)

(73) Assignee: Umicore AG & Co. KG, Hamau-Wolfgang (DE)

(*) Notice: Subject to any disclaimer, the term of this patent is extended or adjusted under 35 U.S.C. 154(b) by 136 days.

(21) Appl. No.: 14/000,962

(22) PCT Filed: Feb. 20, 2012

(86) PCT No.: PCT/EP2012/052878
§ 371 (c)(1),
(2), (4) Date: Oct. 30, 2013

(87) PCT Pub. No.: WO2012/113761
PCT Pub. Date: Aug. 30, 2012

(65) Prior Publication Data
US 2014/0051878 A1    Feb. 20, 2014

(30) Foreign Application Priority Data
Feb. 25, 2011  (DE) .......................... 10 2011 012 515

(51) Int. Cl.
*C07F 15/04* (2006.01)
*C07F 15/00* (2006.01)
(Continued)

(52) U.S. Cl.
CPC ............. *C07F 15/04* (2013.01); *B01J 31/1805* (2013.01); *C07C 257/12* (2013.01);
(Continued)

(58) Field of Classification Search
CPC ............. C07F 5/00; C07F 5/006; C07F 5/063; C07F 5/066; C07F 5/069; C07F 7/00; C07F 7/10; C07F 7/12; C07F 7/28; C07F 15/006; C07F 15/04; B01J 31/1805
USPC .................. 556/1, 43, 52, 137, 140, 175, 407
See application file for complete search history.

(56) References Cited

U.S. PATENT DOCUMENTS 5,502,128 A    3/1996  Flores et al.

FOREIGN PATENT DOCUMENTS

EP    0 210 291 A1    2/1987
JP    2003-531934 (A)   10/2003
(Continued)

OTHER PUBLICATIONS

Romanenko, G.V., et al., "Aminoguanidinium Catlons and the Square-Bipyramidal Hexachlorocuprate(II) Anion in the $(CH_gN_4)_2[CuCl_6]$ Crystal Structure", *Journal of Structural Chemistry*, vol. 35, No. 3, (1994), pp. 317-323.
(Continued)

*Primary Examiner* — Porfirio Nazario Gonzalez
(74) *Attorney, Agent, or Firm* — Brinks Gilson & Lione

(57) ABSTRACT

The invention relates to new metal complexes having N-aminoamidinate ligands, more particularly metal complexes having N,N'-bis(dimethylamino)acetamidinate, N,N'-bis(dimethylamino)formamidinate, N-dimethylaminoacetamidinate or N-dimethylamino-N'-isopropyl-acetamidinate ligands as well as to their preparation and use. The metal complexes are characterized by a five-membered chelate ring. The metal complexes are formed with the metals from the main groups of the PTE, but also with transition-group elements such as tantalum (Ta), iron (Fe), cobalt (Co), nickel (Ni), copper (Cu) or zinc (Zn), and also with precious metals such as palladium (Pd).

The complexes of the invention find use as precursors for the preparation of functional layers by means of gas-phase thin-film processes such as CVD, MO-CVD and ALD. Additionally they may be used as catalysts for olefin hydroamination and for olefin polymerization.

19 Claims, 1 Drawing Sheet

Single-crystal X-ray structure analysis of $In(bdma)Me_2$

(51) Int. Cl.

| | |
|---|---|
| C07F 7/00 | (2006.01) |
| C07F 5/00 | (2006.01) |
| B01J 31/18 | (2006.01) |
| C07C 257/12 | (2006.01) |
| C07C 257/14 | (2006.01) |
| C23C 16/30 | (2006.01) |
| C23C 16/34 | (2006.01) |
| C07F 5/06 | (2006.01) |
| C07F 7/12 | (2006.01) |
| C07F 7/28 | (2006.01) |
| C07F 7/10 | (2006.01) |

(52) U.S. Cl.
CPC ............... *C07C 257/14* (2013.01); *C07F 5/00* (2013.01); *C07F 5/063* (2013.01); *C07F 5/066* (2013.01); *C07F 5/069* (2013.01); *C07F 7/00* (2013.01); *C07F 7/10* (2013.01); *C07F 7/12* (2013.01); *C07F 7/28* (2013.01); *C07F 15/006* (2013.01); *C23C 16/303* (2013.01); *C23C 16/345* (2013.01); *B01J 2231/321* (2013.01); *B01J 2531/0238* (2013.01); *B01J 2531/10* (2013.01); *B01J 2531/30* (2013.01); *B01J 2531/40* (2013.01); *B01J 2531/50* (2013.01)

(56) References Cited

FOREIGN PATENT DOCUMENTS

| | | |
|---|---|---|
| JP | 2004-002305 (A) | 1/2004 |
| JP | 2004-002306 (A) | 1/2004 |
| JP | 2004-506745 (A) | 3/2004 |
| JP | 2008-536800 (A) | 9/2008 |
| WO | WO 2007/124700 A2 | 11/2007 |
| WO | WO 2007/124700 A3 | 11/2007 |
| WO | WO 2007/142700 A1 | 12/2007 |
| WO | WO 2010/071364 A2 | 6/2010 |
| WO | WO 2010/132871 A1 | 11/2010 |

OTHER PUBLICATIONS

Shapiro, Pamela J., et al., "Hydrazido(1-) and 2,2-Dlmethylhydrazido(1-) Derivatives of Permethyiscandocene. Preparaiton and Structural Characterization of their Products from Reactions with Acetonitrile: ($\eta^5$-C$_5$Me$_5$)$_2$ScN(H)C(CH$_3$)NNH$_2$ and ($\eta^5$-C$_5$Me$_5$)$_2$ScN(H)C(CH$_3$)NNMe$_2$", *Inorg. Chem.*, vol. 29, (1990), pp. 4560-4565.
International Search Report for PCT/EP2012/052878, dated Apr. 5, 2012.
Abeysekera, D., et al., "m-Terphenyl-Substituted Amidinates: Useful Ligands in the Preparation of Robust Aluminum Alkyls", *Organometallics*, vol. 20 (2001), pp. 5532-5536.
Albertin, G., et al., "Preparation of mono- and bis-(hydrazine) Complexes of Ruthenium(II)", *J. Chem. Soc. Dalton Trans.*, (1997), pp. 4435-4444.
Albertin, G., et al., "Synthesis, Characterisation and Reactivity of Hydrazine Complexes of Iron(II)", *J. Chem. Soc., Dalton Trans.*, (1997), pp. 4445-4453.
Andrews, M.A,, et al., "Nitration of Alkenes by Palladium Nitro Complexes", *Organometallics*, vol. 3 (1984), pp. 1479-1484.
Bambirra, S., et al., "Yttrium Alkyl and Benzyl Complexes with Amino-Amidinate Monoanionic Ancillary Ligands", *Organornetallics*, vol. 19 (2000), pp. 3197-3204.

Brazeau, A.L., et al., "Synthesis and Thermolysis of Aluminum Amidinates: A Ligand-Exchange Route for New Mixed-Ligand Systems", *Inorganic Chemistry*, vol. 45, No. 5 (2006), pp. 2276-2281.
Bregadze, V.I., et al., "Development of Methods of Synthesis of Volatile Organogallium and Organoindium Compounds used to Prepare Semiconductors", *Journal of Cluster Science*, vol. 13, No. 4 (Dec. 2002), pp. 631-636.
Collins, S., "Polymerization Catalysis with Transition Metal Amidinate and Related Complexes", *Coordination Chemistry Reviews*, vol. 255 (2011), pp. 118-138.
Edelmann, F.T., "Lanthanide Amidinates and Guanidinates: from Laboratory Curiosities to Efficient Homogeneous Catalysts and Precursors for Rare-Earth Oxide Thin Films", *Chem. Soc, Rev.*, No. 38 (2009), pp. 2253-2268.
Gansäuer, A., et al., "A Comparison of Electron Transfer Reagents in the Reductive Opening of Epoxides: Reasons for the Superiority of Titanocene Based Complexes", *Tetrahedron*, vol. 58 (2002), pp. 7017-7026.
Gol'Din, G.S., et al., "Amidrazones and Hydrazidines of Aliphatic Monocarboxylic Acids", *Zhurnal Organicheskoi Khimii*, vol. 5, No. 8, (1969), pp. 1404-1410.
Grundmann, C., et al., "Triazines. XIX. Some Reactions of s-Triazine with Hydrazine and its Organic Derivatives", *J. Am. Chem. Soc.*, vol. 79, No. 11 (1957), pp. 2839-2843.
Hunter, W.H., et al., "The Constitution of Abnormal Ammonium Salts", *Journal of the American Chemical Society*, vol. 54 (1932), pp. 1948-1957.
Kincaid, K., et al., "Synthesis, Structure, and Coordination Chemistry of a Tridentate, Six-Electron-Donor Amidinate Ligand", *Organometallics*, vol. 18 (1999), pp. 5360-5366.
Krajete, A., et al., "Iminohydroxamato Early and Late Transition Metal Halide Complexes—New Precatalysts for Aluminoxane-Cocatalyzed Olefin Insertion Polymerization", *Eur. J. Inorg. Chem.*, (2004), pp. 1740-1752.
Li, Z., et al., "Synthesis and Characterization of Volatile Liquid Cobalt Arnidinates", *J. Chem. Soc. Dalton Trans.*, (2008), pp. 2592-2597.
Li, Z., et al., "Thin. Continuous, and Conformal Copper Films by Reduction of Atomic Layer Deposited Copper Nitride", *Chem. Vap. Deposition*, vol. 12 (2006), pp. 435-441.
Schmidt, J.A.R et al., "Neutral and Cationic Aluminum Complexes Supported by Sterically Bulky Amidinate Ligands", *Organometallics*, vol. 21 (2002), p. 2306-2313.
Sreekumar, C., et al., "A Direct Synthesis of Z-Trisubstituted Allylic Alcohols via the Wittig Reaction", *J. Org. Chem.*, vol. 45 (1980), pp. 4260-4262.
Smith, R.F., et al., "Amidrazones, VII (1a). Formation of s-Triazines by Thermolysis of N[1]-Benzyl-Substituted Amidrazone Ylides", *Journal of Heterocylic Chemistry*, vol. 18 (1981), pp. 319-325.
Sundermeyer, J., et al., "Higher-Valent Derivatives of the d-Metal Acids, 13.-Homoscorpionates as Tripodal Anchoring Ligands of Chloro Functionalized Oxo and Imido Complexes of Elements of Group 5-7", *Chem. Ber.*, vol. 127 (1994), pp. 1201-1212 (English Abstract Included).
Wiberg, K.B., "Bond Dissociation Energies of H$_2$NX Compounds: Comparison with CH$_3$X, HOX and FX Compounds", *J. Phys. Chem.*, vol. 96 (1992), pp, 5800-5803.
Wang, H., et al., "Atomic Layer Deposition of Ruthenium Thin Films from an Amidinate Precursor", *Chem. Vap. Deposition*, vol. 15 (2009), pp. 312-319.
Crimmin, Mark R., et al., "Synthesis and Coordination Chemistry of Tri-Substituted Benzamidrazones", *Dalton Translations*, vol. 40, (published Nov. 25, 2010); pp. 514-522.

Single-crystal X-ray structure analysis of In(bdma)Me$_2$
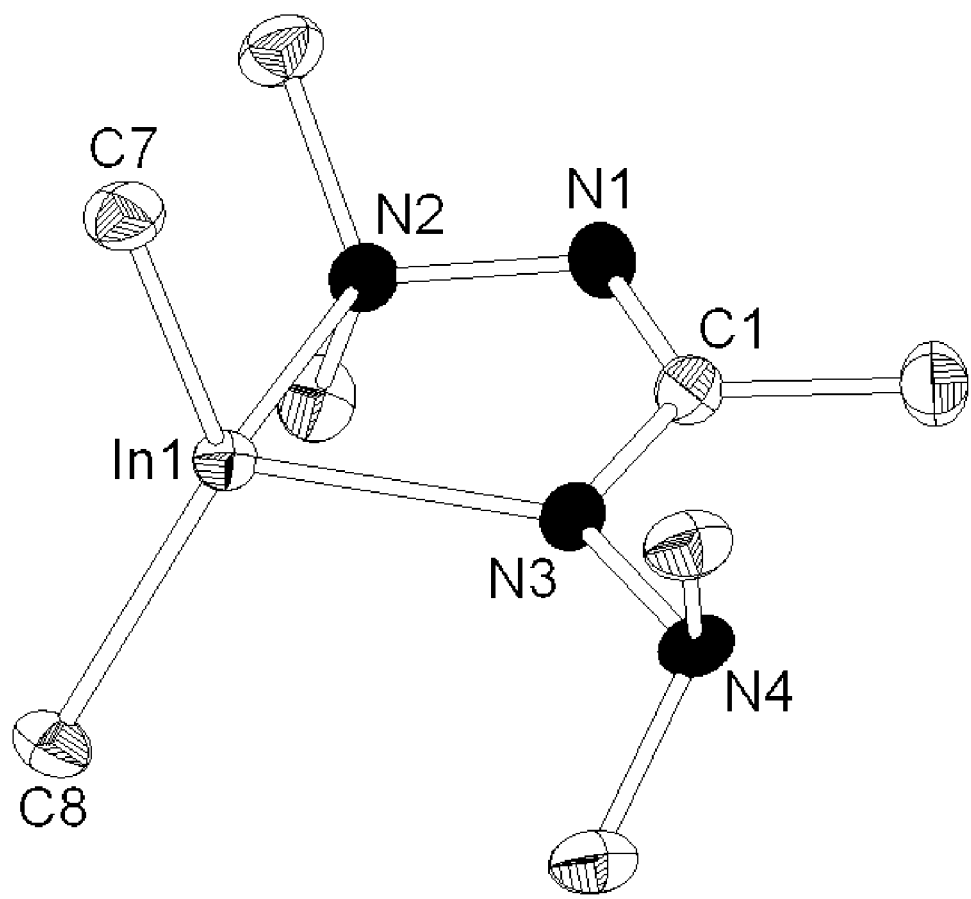

US 9,353,139 B2

METAL COMPLEXES WITH N-AMINOAMIDINATE LIGANDS

This application is a National Stage application of International Application No. PCT/EP2012/052878, filed Feb. 20, 2012. This application also claims priority under 35 U.S.C. §119 to German Patent Application No. 10 2011 012 515.9, filed Feb. 25, 2011.

DESCRIPTION OF THE INVENTION

The present invention relates to new metal complexes having specific N-aminoamidinate ligands, more particularly metal complexes having N-dimethylaminoacetamidinate and N,N'-bis(dimethylamino)acetamidinate and having N,N'-bis (dimethylamino)formamidinate ligands. The invention further relates to the preparation of the metal complexes and also to their use. Metals used are those from group 1 to group 15 of the Periodic Table of the Elements (PTE), more particularly metals from group 13 such as aluminum (Al), gallium (Ga) and indium (In), but also metals of the first transition series such as chromium (Cr), iron (Fe), cobalt (Co) and nickel (Ni) and also the precious metals such as, for example, ruthenium (Ru), palladium (Pd) or platinum (Pt).

The complexes of the invention find use as precursors for producing functional layers by means of gas-phase deposition processes such as CVD (chemical vapour deposition), MO-CVD (metal organic chemical vapour deposition) and ALD (atomic layer deposition). Additionally the complexes find use as catalysts for olefin hydroamination and for olefin polymerization.

Chemical gas-phase deposition (CVD) is a gas-phase reaction (usually on or in the vicinity of the substrate surface). In such reactions, the reaction gases are passed simultaneously into the reaction chamber with the substrate to be coated. The gases, which are usually pre-heated, are activated thermally by the heated substrate, and react with one another. In the course of this reaction, the desired material is deposited and chemically bound (chemisorption).

In addition to countless CVD variants, which differ in operating pressure and other operational parameters, there also exist certain coating processes which represent CVD processes modified to a greater or lesser extert:

In the process known as plasma polymerization, gaseous monomers excited by a plasma form a highly crosslinked layer on a substrate.

Atomic layer deposition (ALD) is a highly modified CVD process, in which the reaction or sorption on the surface stops automatically after the complete covering of the surface. This self-limiting reaction is run in a plurality of cycles (with rinsing steps in between them), thereby achieving very good aspect ratios (length/thickness ratios) and exact layer thicknesses.

Examples of known metal-organic precursors which find use in CVD, MO-CVD and ALD processes are metal-organyl compounds such as trimethylindium ($In(CH_3)_3$), the amido compound $Ti(NMe_2)_4$ or the acetylacetonato complex $[Me_2In(CF_3—CO—CH—CO—CF_3)]$.

The present invention relates to metal complexes having aminoamidinate ligands from the group of the N,N'-bis(dimethylamino)acetamidinate ligands ("bdma"), the (dimethylamino)acetamidinate ligands ("dama"), the N-dimethylamino-N'-isopropyl-acetamidinate ligands ("dapa") and also the N-mono(dimethylamino)acetamidinate ligands ("mdma"), and also from the corresponding series of the formamidinates N,N'-bis(dimethylamino)formamidinate ligands ("bdmf"), the N-(dimethylamino)formamidinate ligands ("damf"), and also the N-mono(dimethylamino)formamidinate ligands ("mdmf"). Preference is given to the metal complexes having N,N'-bis(dimethylamino)acetamidinate ligands ("bdma").

As will be set out further below, this class of ligand is based on an amidinate framework of the type $R^1—C(NR')_2$, where at least one of the two nitrogen atoms is substituted by a further amino group. Preferably both N atoms are substituted by a further amino group. This is the case for the ligand N,N'-bis(dimethylamino)acetamidinate ("bdma").

In the coordinated or complexed state, the ligands are bidentate, with two N atoms being coordinated to the metal and a five-membered ring of sequence M-N—N—C—N— being formed. In the coordinated state, the ligands generally have a singly negative charge (monoanionic structure). Homoleptic and heteroleptic metal complexes may be formed.

The protonated ligands of the N-monoaminoamidines and also N,N'-diaminoamidines are known from the literature. Thus, G. S. Gol'din, et al., Zhurnal Organicheskoi Khimii, 1969, 5, 1404-1410, describe the preparation of the N,N'-diaminoamidines by a reaction of acetimidoethyl ester with an excess of 1,1-dimethylhydrazine (asymmetrically substituted) in the presence of ammonium salts. The analogous monoaminoamidines are obtained by the reaction of acetimidoethyl ester with one equivalent of 1,1-dimethylhydrazine. Subsequently in the further description the preparation of the ligands is addressed.

F. A. Neugebauer (Angew. Chem. 1973, 85, 485-493) described N,N'-diaminoamidine compounds with phenyl radicals on the terminal N atoms, of the type $Ph_2N—N=CH—NH—NPh_2$. The parent structure of N-dimethylaminoamidine was prepared (as the HCl salt) for the first time by Neunhoeffer et al. (cf. H. Neunhoeffer, H. Hennig, Chem. Ber. 1968, 101, 3947-3951).

The present invention relates to new metal complexes, disclosed here for the first time, having N-aminoamidinate ligands.

Monoanionic N-organoaminoamidinate ligands and their metal complexes are described in the literature (cf. S. Bambirra et al., Organometallics, 2000, 19, 3197-3204). These complexes possess a $(CH_2)_n$— spacer group (n=2, 3) between the amidinate nitrogen atom and the amino nitrogen atom, and so the amino group is not bonded directly to the amidinate nitrogen. These metal complexes have a six-membered ring structure (where both the amidinate group and the terminal amino group are bonded to the central atom and form a six-membered ring). The compounds are used for catalytic applications.

U.S. Pat. No. 5,502,128 describes N-organoamidinate complexes with metals from transition group 4, and their use in polymerization processes. The complexes having the N-organoamidinate ligands of type $RC(NR')_2$ have a 4-membered structure. N-Amino-substituted amidinate complexes are not described.

WO 2007/124700 discloses polycyclic N-organoamidinate complexes of Cu(I), which are used for producing thin copper layers by means of CVD. N-Amino-substituted amidinate complexes are not described.

The existing metal complexes with amidinate ligands contain two organic carbon radicals on the amidinate nitrogen atoms. This leads in general, in the coordinated metallated state, to a four-membered strained chelate ring structure. One typical example is the homoleptic Co(II)-amidinate complex [Co(N,N'-diisopropylacetamidinato)$_2$] (cf. Gordon et al., J. Chem. Soc. Dalton Trans., 2008, 2592-2597) or the aluminium amidinate complexes of the type [(MeC(NCH (CH₃)₂)₂)AlEt₂] and [(EtC(NCH(CH₃)₂)₂)AlMe₂] (cf. A. L. Brazeau et al., *Inorg. Chem.* 2006, Vol. 45, No. 5, 2276-2281).

Similar complexes are described by R. G. Gordon et al. Thus, Cu nitride is deposited from a Cu(I) complex with N,N'-di-sec-butylacetamidinate (*Chem. Vap. Dep.*, 2006, 12, 435-441), and thin ruthenium films are prepared by means of ALD using the precursor [Ru(II)(CO)₂(N,N'-di-tertbutylacetamidinate)₂] (cf. *Chem. Vap. Deposition*, 2009, 15, 312-319).

The metal complexes having at least one N-aminoamidinate ligand that are provided by the present specification have at least one aminyl radical —NR₂ and not more than two aminyl radicals bonded instead of the carbon radicals, via direct N—N bonding, to the amidinate nitrogen atoms N and N'. This particular design results in a particularly privileged five-ring chelate structure in the storable precursor complexes and in thermal predetermined breakage sites in the ligand framework (the N—N bonds), which initiate the decomposition of the precursors even at advantageously low decomposition temperatures.

In the fabrication of semiconductor components (processors, memory chips, sensor chips etc.) it is usual for the deposition of metallic, oxidic and nitridic layers to employ CVD, MO-CVD and ALD processes. These processes have now acquired great significance in semiconductor technology and microelectronics.

In these processes, the substrate is coated at the interface between substrate and gas phase by vaporization and heating of a suitable precursor compound above the decomposition point, often in the presence of a reactive gas (such as hydrogen, ammonia or 1,1-dimethylhydrazine). Processes of these kinds are used, for example, to generate layers of GaN, InN, TaN, TiN or Si₃N₄. It is also possible to deposit metallic layers (for example Pd, Ru or Co). In order to be suitable for use in CVD and ALD, the appropriate ligands and metal complexes ought to possess a molecular construction (and should ideally be present as monomer), possess a low molar mass, and have a high volatility and a low decomposition point at temperatures above the storage temperature.

Furthermore, they ought to be thermally stable at room temperature, so that there is no decomposition prior to the deposition process. In addition, the compounds ought to possess a uniform, reproducible decomposition mechanism, and ought to have suitable predetermined breakage points for the fragmentation in the molecule. Lastly, with a defined precursor compound under identical CVD conditions, it ought always to be possible to deposit the same layer with consistent quality.

Suitable ligands for such precursor compounds ought to provide good steric shielding of the metal centre, be electron-rich, and ought electronically to satisfy the metal centre, thereby lowering the Lewis acidity and inhibiting the aggregation of the compounds into coordination polymers of low volatility. During the deposition, furthermore, a reduction of the metal centre is frequently necessary. Ligands which feature a high proportion of hydrazine structural units, such as the ligands of the invention, carry reduction equivalents with them per se.

The existing metal complexes with amidinate ligands have disadvantages. They possess, for instance, no uniform, defined decomposition pathway; the metal atom is generally incompletely shielded and possesses a relatively low electron density. The use of these amidinate complexes, particularly in the case of thin-film deposition processes, may therefore lead to disadvantages in respect of reproducibility, layer quality, deposition rate and yield.

It is an object of the present invention, therefore, to provide improved metal amidinate complexes. These new amidinate complexes ought to be suitable for use in thin-film deposition processes. Furthermore, they ought also to be useful in catalyst processes.

This object is achieved by the new N-aminoamidinate complexes in accordance with the present claims.

The metal complexes of the invention having at least one N-aminoamidinate ligand, possess the general formula 1

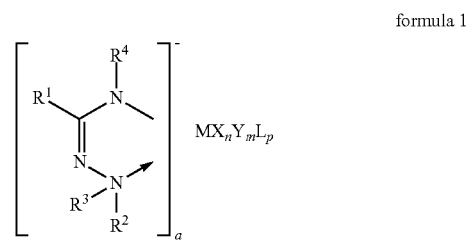

formula 1 wherein

M is a metal from groups 1 to 15 of the Periodic Table of the Elements (PTE), $R^1$ is hydrogen or a cyclic, linear or branched alkyl radical having up to 8 C atoms, or a substituted or unsubstituted aryl radical having up to 20 C atoms, $R^2$ and $R^3$ independently of one another are hydrogen, $CH_3$ or $C_2H_5$ $R^4$ is hydrogen or a cyclic, linear or branched alkyl radical having up to 8 C atoms, $NH_2$, $N(CH_3)_2$ or $N(C_2H_5)_2$.

In a further embodiment, the radical $R^4$ is hydrogen, $CH_3$, $NH_2$, $N(CH_3)_2$, or $N(C_2H_5)_2$. In a specific embodiment, the radical $R^4$ is isopropyl ($CH(CH_3)_2$).

X is a monoanionic co-ligand selected from the hydride anion (H⁻), from the group of the halides, from the group of the cyclic, linear or branched alkylide radicals having up to 8 C atoms, from the group of the substituted or unsubstituted arenide and heteroarenide radicals having up to 10 C atoms, from the group of the alkoxylato ligands, from the group of the alkylthiolato or alkylselenato ligands or from the group of the secondary amido ligands, Y is a dianionic co-ligand selected from the oxo group [O]²⁻ or the imido group [NR⁵]²⁻, where R⁵ is a cyclic, branched or linear alkyl radical having up to 8 C atoms or is a substituted or unsubstituted aryl radical having up to 20 C atoms, L is a neutral 2-electron donor ligand, a is an integer between 1 and 4 and n, m and p each independently of one another are 0, 1, 2, 3 or 4.

The invention relates more particularly to metal complexes having at least one N-aminoamidinate ligand from the group of the N,N'-bis(dimethylamino)acetamidinate ligands ("bdma"), the (dimethylamino)acetamidinate ligands ("dama"), and also the mono(dimethylamino)acetamidinate ligands ("mdma"), and also from the corresponding series of the formamidinates N,N'-bis(dimethylamino)formamidinate ligands ("bdmf"), the N-(dimethylamino)formamidinate ligands ("damf"), and also the mono(dimethylamino)formamidinate ligands ("mdmf"). Preference is given to the metal complexes having at least one N,N'-bis(dimethylamino)acetamidinate ligand ("bdma").

In the complexes of the invention the metal atom may be present in the formal oxidation states from +1 to +6. Preferred oxidation states are +1, +2 and +3. In the majority of cases the N-aminoamidinate ligand carries a negative charge and is therefore in monoanionic form.

The central atom M used in the complexes is a metal from groups 1 to 15 of the Periodic Table of the Elements (PTE). This encompasses the metals of the s block (groups 1 and 2, i.e. alkali metals and alkaline earth metals), the metals of the p block (groups 13, 14 and 15) and the metals of the d block (transition metals from groups 3 to 12) of the PTE. This definition also encompasses, of course, all metals within the periods of the PTE, hence including the precious metals.

Preference is given to using metals and semi-metals of groups 13, 14, and 15 of the Periodic Table of the Elements (PTE). Particularly preferred are the metals aluminum (Al), gallium (Ga), indium (In), silicon (Si), germanium (Ge), tin (Sn), arsenic (As) and antimony (Sb).

It is also possible to use transition metals from groups 3, 4, 5, 6, 7, 8, 9, 10, 11 and 12 of the PTE. Particularly preferred here are the metals titanium (Ti), zirconium (Zr), hafnium (Hf) and chromium (Cr), manganese (Mn), iron (Fe), cobalt (Co) and nickel (Ni), zinc (Zn) and copper (Cu).

The term "precious metals" encompasses the 8 metals ruthenium (Ru), rhodium (Rh), palladium (Pd), osmium (Os), iridium (Ir), platinum (Pt), silver (Ag) and gold (Au). Of these, ruthenium (Ru), rhodium (Rh), palladium (Pd) and platinum (Pt) are preferred. Palladium complexes are particularly preferred.

The radical $R^1$ is hydrogen or a cyclic, linear or branched alkyl radical having up to 8 C atoms or is a substituted or unsubstituted aryl radical having up to 20 C atoms. Preferred alkyl radicals are $CH_3$ and $C_2H_5$, preferred aryl radicals are phenyl ($C_6H_5$), tolyl, 2,6-diisopropylphenyl and 2,4,6-trimethylphenyl (mesityl).

The radicals $R^2$ and $R^3$ independently of one another are hydrogen, $CH_3$ or $C_2H_5$; the radical $R^4$ is hydrogen or a cyclic, linear or branched alkyl radical having up to 8 C atoms, $NH_2$, $N(CH_3)_2$ or $N(C_2H_5)_2$. In a further embodiment, the radical $R^4$ is hydrogen, $CH_3$, $NH_2$, $N(CH_3)_2$, or $N(C_2H_5)_2$. In a specific embodiment, the radical $R^4$ is isopropyl ($CH(CH_3)_2$).

The radical X is a monoanionic co-ligand selected from the hydride anion ($H^-$), or from the group of the halides ($F^-$, $Cl^-$, $Br^-$ or $F^-$), or from the group of the cyclic, linear or branched alkanide radicals (i.e. carbanionic radicals) having up to 8 C atoms (such as, for example, methylide ($CH_3^-$), ethylide ($C_2H_5^-$), isopropylide (iso-$C_3H_7^-$) or tert-butylde (tert-$C_4H_9^-$)), or from the group of the substituted or unsubstituted arylide and heteroarylide radicals having up to 10 C atoms (such as, for example, the phenylide anion ($C_6H_5^-$), or the ortho-, meta-, para-tolylide anion [$C_6H_4(CH_3)$]$^-$, thiophen-2-ylide anion ($C_4H_3S^-$)) or from the group of the anionic alkoxylate ligands (such as, for example, methylate (MeO$^-$), ethylate (EtO$^-$), tert-butylate (tert-BuO$^-$)), or from the group of the anionic alkylthiolate and alkylselenate ligands (such as, for example, MeS$^-$, MeSe$^-$, (tert-Bu)S$^-$ or (tert-Bu)Se$^-$)) or from the group of the anionic secondary amide ligands (such as, for example, dimethylamide (NMe$_2^-$), diethylamide (NEt$_2^-$), methylethylamide (NMeEt$^-$) or N-pyrrolidide [NC$_4$H$_8$]$^-$).

The radical X is preferably the hydride anion ($H^-$), chloride ($Cl^-$), bromide ($Br^-$), methylide ($CH_3^-$), ethylide ($C_2H_5^-$), dimethylamide (NMe$_2^-$) and diethylamide (NEt$_2^-$).

The radical Y is a dianionic coligand, such as, for example, the oxo group [O]$^{2-}$ or the imido group [NR$^5$]$^{2-}$, where R$^5$ is a cyclic, branched or linear alkyl radical having up to 8 C atoms or is a substituted or unsubstituted aryl radical having up to 20 C atoms. Preference is given to the imido group [N$^t$Bu]$^{2-}$.

The radical L is a neutral 2-electron donor ligand. Neutral 2-electron donor ligands L are all neutral electron-pair donor molecules; examples are pyridine, dioxane, $NH_3$, THF, CO and also alkylphosphines (such as PMe$_3$ or PCy$_3$) or arylphosphines such as PPh$_3$. Preference is given to the ligands pyridine, CO and $NH_3$.

In a further embodiment of the invention, the complexes of the formula 1 according to the invention may be present in the form of ligand-bridged dimers. The bridging in this case may be via the groups X (that is, for example, via halogen bridges and/or hydrogen bridges). In general, coordinative saturation of the metal atom is achieved by this means. One example of this class of complex is the dimeric Al complex [Al(bdma)H (μ-H)]$_2$, in which hydridic hydrogen bridges are present. These metal complexes are characterized in that they have a dimeric structure with bridging ligand functions X, Y or L.

In a further embodiment of the present invention, the N-aminoacetamidine or the N-aminoformamidine may also be coordinated in the protonated neutral form to the metal atom. In this case the metal-Lewis acid is reacted directly with the neutral chelate ligands. These complexes have the following general formula 2.

formula 2

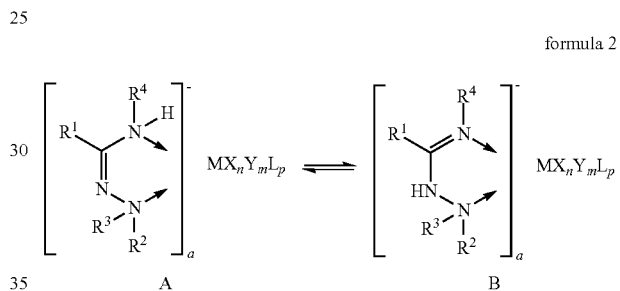

In formula 2 the hydrogen atom is mobile. In such complexes of the protonated (neutral) N-aminoamidine ligands, accordingly, it is possible for two tautomers A and B to form, and either A or B may have the higher proportion in the equilibrium.

Furthermore, in formula 2

M is a metal from groups 1 to 15 of the Periodic Table of the Elements (PTE), $R^1$ is hydrogen or a cyclic, linear or branched alkyl radical having up to 8 C atoms, or a substituted or unsubstituted aryl radical having up to 20 C atoms, $R^2$ and $R^3$ independently of one another are hydrogen, $CH_3$ or $C_2H_5$, $R^4$ is hydrogen, $CH_3$, $NH_2$, $N(CH_3)_2$ or $N(C_2H_5)_2$, X is a monoanionic co-ligand selected from the hydride anion ($H^-$), from the group of the halides, from the group of the cyclic, linear or branched alkylide radicals having up to 8 C atoms, from the group of the substituted or unsubstituted arylide and heteroarylide radicals having up to 10 C atoms, from the group of the alkoxylato ligands, from the group of the alkylthiolato or alkylselenato ligands or from the group of the secondary amido ligands, Y is a dianionic coligand selected from the oxo group [O]$^{2-}$ or the imido group [NR$^5$]$^{2-}$, where R$^5$ is a cyclic, branched or linear alkyl radical having up to 8 C atoms or is a substituted or unsubstituted aryl radical having up to 20 C atoms, L is a neutral 2-electron donor ligand, a is an integer between 1 and 4 and n, m and p each independently of one another are 0, 1, 2, 3 or 4.

In one particularly preferred embodiment of the present invention, N,N'-bis(dimethylamino)acetamidine ("H-bdma") is bonded as neutral ligand to the metal (formula 3).

formula 3

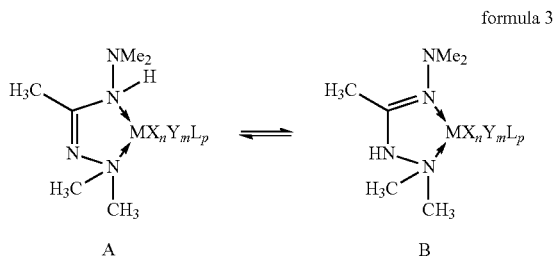

This embodiment of the complexes of the invention is observed more particularly for the metals from groups 5 and 11 of the PTE. Examples of the complexes of the formula 3 are the compounds Ta(N$^t$Bu)Cl$_3$(Hbdma) (cf. Example 12), Nb(N$^t$Bu)Cl$_3$(Hbdma) and [CuCl(Hbdma)].

In a further embodiment of the complexes of the invention, monoanionic N-aminoamidinate ligands represented by index c and neutral N-aminoamidine ligands represented by index b are combined simultaneously in one complex and on one coordination centre (formula 4).

formula 4

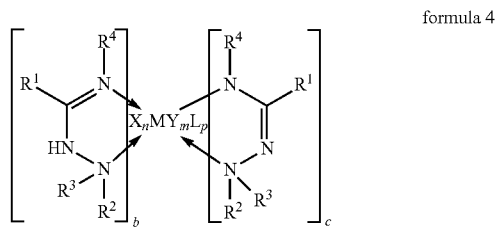

The indices b and c in formula 4 independently of one another are integers 1, 2 or 3. The remaining groups X, Y and L and also the indices n, m and p are defined as in formula 1.

In this embodiment of the present invention, for example the monoanionic bdma ligand and also the neutral ligand N,N'-bis(dimethylamino)acetamidine ("H-bdma") may be coordinated to the same metal atom. Metal complexes featuring these ligand combinations have particular advantages in respect of steric shielding.

Surprisingly it was found that the introduction of at least one further amino group on the two N-atoms of the amidinate ligand leads to advantageous properties in the metal complexes comprising this ligand. In the N-aminoamidinate complexes of the invention, the five-membered ring chelate structure provides better steric shielding and suffers less from ring strain and thus is stabilizing the storage form of these precursors (in the ground state). This feature is favourably combined with the greater ease of disintegration, i.e. the dissociation of the N—N bond in the thermally excited state.

In particular it was found that replacing the alkyl radicals on the nitrogen atoms of the conventional N-organoamidinate ligands known from the literature, by at least one N-amino substituent (—NR$^2$R$^3$) increases the electron density of the ligand. At the same time, a hydrazine unit is introduced and hence reduction equivalents are present, which have advantageous consequences for the reductive cleavage of the molecule. Moreover, with the weak N—N single bond in the ligand, a predetermined breakage point has been introduced. If the ligand is coordinated to the metal atom, the easy thermal dissociation of the N—N bond of the chelate ring may bring about more rapid fragmentation of the overall metal complex. These facts are supported by literature details. According to K. B. Wiberg (*J. Phys. Chem.* 1992, 96, 5800-5803), the dissociation energy of the N—N bond in hydrazine (H$_2$N—NH$_2$) is 63.9 kcal/mol, whereas the dissociation energy of the N—C bond in methylamine (H$_2$N—CH$_3$) is about 82.9 kcal/mol, in other words around 30% higher. New and easy fragmentation pathways are opened up which do not exist for N-organoamidinate complexes known from the literature, owing to the strong N—C bond. Indications of the decomposition pathway via the easy N—N bond cleavage in the complexes of the invention is provided by the mass spectra, whereby nitrogen radical cations with m/z=44 (corresponding to N(CH$_3$)$_2^+$) are found. As a result of these new disintegration pathways, there is less unwanted incorporation of carbon into the deposited metallic and/or ceramic layers of the type M$_x$N$_y$, as it is the case when using the conventional N-organoamidinate complexes. When the metal complexes of the invention are employed in gas-phase thin-film epitaxy it becomes possible in many cases to work without the use of additional reducing reactive gases such as hydrogen, ammonia and hydrazine in the CVD deposition process. This results in layers of high purity, which can be deposited in reproducible quality.

Addressed below first of all is the general preparation of the amidinate ligands. Described below are the five most important types of ligand, the form shown in each case being the monoanionic form of the ligands, in which they are frequently bonded in the metal complexes of the invention.

a) N,N'-bis(dimethylamino)acetamidinate ("bdma", formula 5)

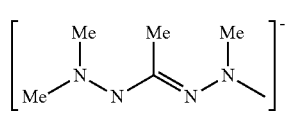

b) mono(dimethylamino)acetamidinate ("mdma", formula 6)

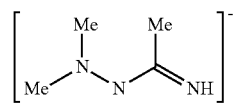

c) N-dimethylamino-N' methylacetamidinate ("dama", formula 7)

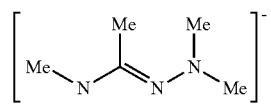

d) N,N'-bis(dimethylamino)formamidinate ("bdmf", formula 8)

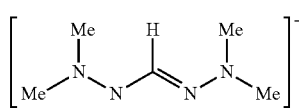

e) N-dimethylamino-N'-iso-propylacetamidinate ("dapa", formula 9)

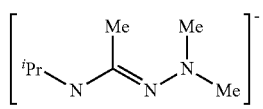

The respective neutral ligands possess an additional proton on the free electron pair of the divalent N atom.

The class of compound to which the uncharged ligand molecule "H-bdma" belongs is also referred to in the literature as hydrazidine or dihydroformazane. The name selected in this specification, N,N'-bis(dimethylamino)acetamidine, is intended to show the analogy to the amidines. This neutral ligand is abbreviated herein by the designation "H-bdma". Correspondingly the monoanionic ligand is present as N,N'-bis(dimethylamino)acetamidinate and is designated using the abbreviation "bdma".

The bis(dimethylamino)acetamidinate ligand is prepared in a modification of the literature method of Gol'din (G. S. Gol'din, et al., *Zhurnal Organicheskoi Khimii*, 1969, 5, 1404-14109). The Gol'din synthesis represents in principle a three-step procedure, in which there is a reaction of ethanol with acetonitrile to give the acetimidoethyl ester hydrochloride, a deprotonation of the acetimidoethyl ester hydrochloride is carried out to give the free base acetimidoethyl ester, and subsequently the free base acetimidoethyl ester is reacted with 1,1-diorganohydrazine to give the desired hydrazidine.

In a variation of the Gol'din synthesis, in the preparation of H-bdma by the process of the present specification, the resulting HCl salt of the acetimidoethyl ester is not deprotonated and isolated, it is instead reacted directly (in the presence of a base such as, for example, triethylamine) with two equivalents of 1,1-dialkylhydrazine, resulting in a two-stage procedure.

Equation 1

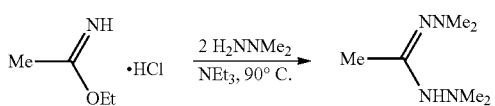

The process of the present specification is composed of the steps (a) reaction of ethanol with acetonitrile in the presence of dry, gaseous hydrogen chloride to give the acetimidoethyl ester hydrochloride and (b) reaction of the acetimidoethyl ester hydrochloride with 1,1-dialkylhydrazine in triethylamine.

Solvents used are amines such as, for example, triethylamine; the reaction takes place at temperatures in the range from 60 to 100° C. After the end of the reaction, the components are separated by fractional distillation. The modified process has broad applicability; it is also possible to prepare the amidinates with other substituents. In that case, for example, 1,1-dimethylhydrazine or 1,1-diethylhydrazine is used.

The neutral ligand mono(dimethylamino)acetamidine ("H-mdma") is prepared in a largely analogous way to the instructions given by Gol'din. The reaction of acetimidoethyl ester hydrochloride with one equivalent of 1,1-dimethylhydrazine and triethylamine is carried out in chlorinated solvents such as dichloromethane.

The neutral ligand N-dimethylamino-N'-methylacetamidine ("H-dama") is prepared in accordance with literature instructions by R. F. Smith et al., *Journal of Heterocyclic Chemistry* 1981, 18, 319-325. The preparation is based on an in situ O-alkylation of N-methylacetamide with dimethyl sulphate, followed by reaction with one equivalent of 1,1-dimethylhydrazine:

Equation 2

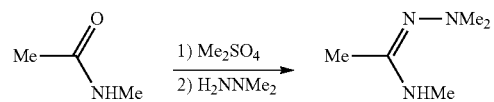

The amidinate complexes of the invention can be prepared by various synthesis pathways. While the neutral ligands can be prepared under air, the metal complexes must be prepared under inert gas (argon, nitrogen).

The formamidinate ligand of the invention, N,N'-bis(dimethylamino)formamidine "H-bdmf", is prepared in accordance with literature instructions from Ch. Grundmann, A. Kreutzberger, *J. Am. Chem. Soc.* 1957, 79 (11), 2839-2843 by reaction of 1,3,5-triazine with 1,1-dimethylhydrazine.

The most important synthesis routes involve an alkane or amine elimination (cf. the preparation of the complex (bdma)AlMe$_2$, cf. Example 2 and Equation 3:

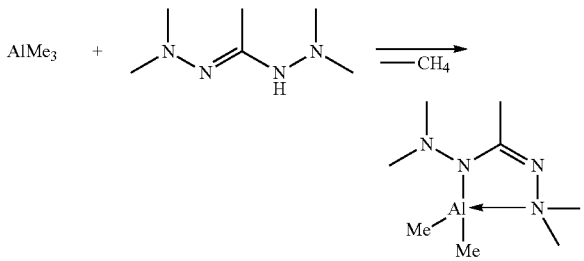

Equation 3 A further preparation route involves a salt elimination after prior deprotonation of the neutral ligand. In this case, first of all the Li salt or K salt of the ligand is generated (using $^n$BuLi, lithium hexamethyldisilazide, LiHMDS or potassium hexamethyldisilazide, KHMDS) and is subsequently reacted with the metal compound under inert gas (cf. the preparation of the complex (bdma)GaCl$_2$ in Example 4 and Equation 4:

Equation 4

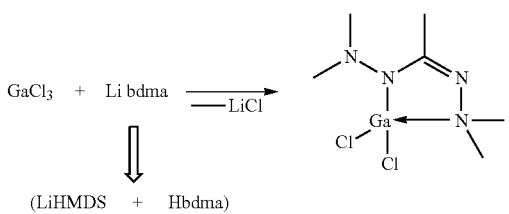

The amidinate complexes of the invention are generally prepared in a "one-pot reaction", with the metal starting compound being introduced and the amidine/amidinate ligand added. Depending on the type of starting compound, the reaction may be carried out in a very broad temperature range from −78° C. (cooling with dry ice) up to 100° C. The reaction times are typically in the range from 30 minutes to 48 hours, in some cases they can be extended to 72 hours. Solvents used include aliphatic solvents (such as, for example, pentane, hexane, heptane), aromatic solvents (benzene, toluene), chlorinated solvents (dichloromethane, chloroform), ethereal solvents (diethyl ether, tetrahydrofuran) or alcohols (methanol, ethanol, isopropanol). The metal complex of the invention can be isolated by crystallization, sublimation, concentration and/or precipitation. In this case the separation techniques employed are those known to the skilled person (e.g. filtration, centrifugation, etc). Further details may be taken from the examples below.

EXPERIMENTAL SECTION/EXAMPLES

Abbreviations
$^n$Bu: n-butyl, —CH$_2$CH$_2$CH$_2$CH$_3$
$^t$Bu: tert-butyl, —C(CH$_3$)$_3$
$^i$Pr: iso-propyl, —CH(CH$_3$)$_2$
Et: ethyl, —CH$_2$CH$_3$
Me: methyl, —CH$_3$
Hbdma: N,N'-bis(dimethylamino)acetamidine
Hdama: N-dimethylamino-N' methylacetamidine
Hdapa N-dimethylamino-N' isopropylacetamidineHbdmf N,N'-bis(dimethylamino)formamidine
Hmdma: N-monodimethylaminoacetamidine
HMDS: hexamethyl disilazide, N(SiMe$_3$)$_2$$^-$
MHz: megahertz, $10^6$ s$^{-1}$
ppm: parts per million, unit of chemical shift in NMR spectroscopy
THF: tetrahydrofuran
TMS: trimethylsilyl, —SiMe$_3$
TMSCl trimethylsilyl chloride
For the multiplicities in the NMR spectra the abbreviations are as follows:
S: singlet
bs: broad singlet
d: doublet
t: triplet
m: multiplet
Intensities in the IR spectra are abbreviated as follows:
w: weak
m: moderately strong
s: strong
vs: very strong
General Remarks The syntheses of the neutral ligands do not require inert-gas operation; the chemicals as well are used without preliminary drying or purification. Due to the toxicity potertial of the hydrazine derivatives, however, contact of any kind must be avoided.

The preparation of the lithium and potassium salts of the ligands and also the synthesis of metal complexes of the invention must be carried out with exclusion of oxygen and moisture; furthermore due to the use of pyrophoric substances, dried, anhydrous solvents must be used. Solvents are dried using suitable drying agents and are stored under a nitrogen atmosphere.

The chemicals used are available commercially: $^t$butylamine (Merck-Schuchardt), $^n$butyllithium in hexane solution (CheMetall), dimethylamine (Merck-Schuchardt), N,N-dimethylhydrazine (Aldrich), dimethyl sulphate (Sigma-Aldrich), iron(II) chloride (Aldrich), gallium trichloride (Strem), hafnium tetrachloride (Aldrich), hexamethyldisilazane (Fluka), lithium aluminium hydride (Aldrich), lithium hydride (Aldrich), lithium dimethylamide, LiN(CH$_3$)$_2$ (Aldrich), magnesium sulphate (anhydrous, Sigma-Aldrich), N-methylacetamide (Fluka), sodium hydroxide (Sigma-Aldrich), palladium dichloride (ABCR), pyridine (Grüssing), tantalum pentachloride (H. C. Starck), titanium tetrakisdimethylamide (ChemPur), triethylamine (Sigma-Aldrich), trimethylsilyl chloride (Acros), vanadium(III) chloride (Merck).

The following starting compounds are synthesized or are obtainable in accordance with the literature instructions specified:

Lithium hexamethyldisilazide, LiN(Si(CH$_3$)$_3$)$_2$: U. Wannagat, H. Niederprum, *Chem. Ber.* 1961, 94, 1540-1547.

Potassium hexamethyldisilazide, KN(Si(CH$_3$)$_3$)$_2$: C. Sreekumar, K. P. Darst, W. C. Still, *J. Org. Chem.* 1980, 45, 4260-4262.

Palladium dichloride bisacetonitrile, [PdCl$_2$(CH$_3$CN)$_2$]: M. A. Andres, T. C. T. Chang, C. W. F. Cheng, L. V. Kapustay, K. P. Kelly, M. J. Zweifel, *Organometallics* 1984, 3, 1479-1484.

Tantalum tert-butylimidotrichlorobispyridine, [Ta(NtBu) Cl$_3$py$_2$]: J. Sundermeyer, J. Putterlik, M. Foth, J. S. Field, N. Ramesar, *Chem. Ber.* 1994, 127, 1201-1212.

Trimethylammonium chloride, Me$_3$N—HCl: W. H. Hunter, G. D. Byrkit, *Journal of the American Chemical Society* 1932, 54, 1948-1957.

Trimethylgallium, Ga(CH$_3$)$_3$: V. I. Bregadze, L. M. Golubinskaya, B. I. Kozyrkin, *Journal of Cluster Science* 2002, 13, 631-636.

Trimethylindium, In(CH$_3$)$_3$: V. I. Bregadze, L. M. Golubinskaya, B. I. Kozyrkin, *Journal of Cluster Science* 2002, 13, 631-636.

Vanadium trichloride tristetrahydrofuran, [VCl$_3$(THF)$_3$]: A. Gansaeuer, B. Rinker, *Polyhedron* 2002, 7017-7026.

For NMR spectra, instruments of the types AVANCE 300 A, AVANCE 300 B and DRX 500 from Bruker were used; mass-spectrometric investigations took place on an instrument of type MAT95 from Finnigan; elemental analyses were carried out on instruments from Heraeus of the CHN-Rapid type. The IR spectra were recorded using a Bruker instrument (instrument type ALPHA).

Preparation of the Neutral Ligands a) Hbdma: In 150 ml of triethylamine, 51 g (65.4 ml, 0.85 mol, 2.33 equivalents) of N,N-dimethylhydrazine are introduced and are admixed, in portions at room temperature, with vigorous stirring with 45 g (0.36 mol, 1.00 equivalent) of acetimidoethyl ester hydrochloride, after which the evolution of a gas is observed. After two hours of stirring, the colourless suspension is heated to 90° C. and stirred at this temperature for four hours. Following filtration on a Buechner funnel, the volatile constituents are distilled off under atmospheric pressure. The oil which remains is distilled under subatmospheric pressure (88° C./88 mbar). The product is obtained as a colourless liquid. Yield: 39.4 g (0.27 mol, 75%).

$^1$H NMR (C$_6$D$_6$, 300.1 MHz, 300 K): δ (in ppm)=2.04 (s, 6 H, NMe$_2$), 2.05 (s, 3 H, MeC), 2.46 (s, 6 H, NMe$_2$), 6.54 (bs, 1 H, NH).

HR-EI-MS: calculated for C$_6$H$_{16}$N$_4$: 144.1375 m/z. found: 144.1371 m/z.

IR: about 3250 (vw), 2978 (w), 2946 (w), 2853 (w), 2817 (w), 2771 (w), 1625 (vs), 1398 (m), 1159 (m), 1016 (m), 962 (m), 908 (m).

b) Hmdma: 7.50 g (60.69 mmol, 1.00 equivalent) of acetimidoethyl ester hydrochloride are dissolved in 150 ml of dichloromethane and admixed dropwise at 0° C. with a mixture of 4.00 g (66.56 mmol, 1.10 equivalents) of N,N-dimethylhydrazine and 6.76 g (66.56 mmol, 1.10 equivalents) of triethylamine. The reaction mixture is warmed slowly to room temperature overnight, with stirring, and then the volatile constituents are distilled off under atmospheric pressure. The yellowish solid which remains is introduced into a two-phase mixture of 50 ml of dichloromethane and 50 ml of a solution of 4.00 g of NaOH in $H_2O$, and the mixture is stirred intensively for two hours. The organic phase is separated off and the aqueous phase is extracted with three times 10 ml of dichloromethane. The combined organic phases are dried over $MgSO_4$ and then the solvent is removed on a rotary evaporator. The solid which remains is recrystallized from hot hexane, and the product is obtained, after drying under a fine vacuum at room temperature, in the form of fibrous crystals. Yield: 4.23 g (41.88 mmol, 69%). Melting point: 73° C. (literature value: 68-73° C.).

c) Hdama: 8.80 g (120.40 mmol, 1.00 equivalent) of N-methylacetamide are admixed with 15.18 g (120.40 mmol, 1.00 equivalent) of dimethyl sulphate and the mixture is heated at 60° C. for two hours. After cooling to room temperature, the reaction mixture is washed with three times 20 ml of diethyl ether, and the residues of ether are briefly removed by applying a fine vacuum. The oil which remains is dissolved in 50 ml of methanol and admixed at 0° C. with a mixture of 7.96 g (132.44 mmol, 1.10 equivalents) of N,N-dimethylhydrazine and 13.38 g (132.44 mmol, 1.10 equivalents) of triethylamine. The reaction mixture is warmed slowly to room temperature overnight with stirring, after which the solution is introduced into a two-phase mixture of 50 ml of dichloromethane and 50 ml of a solution of 6 g of NaOH in 50 ml of water. Following separation of the phases, the aqueous phase is extracted with four times 25 ml of dichloromethane. Drying over $MgSO_4$, distillation under atmospheric pressure and subsequent distillation at 65° C./50 mbar give 9.00 g (78.26 mmol, 65%) of the product as a colourless liquid.

$^1$H NMR (CDCl$_3$, 300.1 MHz, 300 K): δ (in ppm)=1.79 (s, 3 H, MeC), 2.24 (s, 6 H, NMe$_2$), 2.76 (s, 3 H, NMe), 5.89 (s, 1 H, NH).

$^{13}$C NMR (CDCl$_3$, 75.5 MHz, 300 K): δ (in ppm)=17.0 (MeC), 29.2 (NMe), 46.5 (NMe$_2$), 159.2 (MeC).

d) Hdapa: 10.39 g (102.70 mmol, 1.00 equivalent) of N-iso-propylacetamide are admixed with 9.8 mL (103.30 mmol, 1.00 equivalent) of dimethyl sulphate and the mixture is heated at 60° C. for 23 hours. After cooling to room temperature, the reaction mixture is washed twice with 10 mL of diethyl ether, and the residues of ether are briefly removed by applying a fine vacuum. The oil which remains is dissolved in 100 mL of iso-propanol and admixed at room temperature with a solution of 9.0 mL (116.80 mmol, 1.14 equivalents) of N,N-dimethylhydrazine and 16.0 mL (115.40 mmol, 1.13 equivalents) of triethylamine in 25 mL of iso-propanol. The reaction mixture is stirred for 60 hours, after which the solvent is removed under reduced pressure. The remaining yellow oil is dissolved in 50 mL of dichloromethane and a solution of 8.40 g (150 mmol, 1.50 equivalents) of potassium hydroxide in 15 mL of water is added slowly. Following separation of the phases, the aqueous phase is extracted twice with 15 mL of dichloromethane. Drying over $MgSO_4$, distillation under atmospheric pressure and subsequent distillation at 52° C./5 mbar give 7.13 g (49.90 mmol, 48%) of the product as a colourless liquid.

$^1$H NMR (CDCl$_3$, 300.1 MHz, 300 K): δ (in ppm)=1.14 (d, $^3J_{HH}$=6.4 Hz, 6 H, CHMe$_2$), 1.88 (s, 3 H, MeC), 2.31 (s, 6 H, NMe$_2$), 3.57 (sept, $^3J_{HH}$=6.4 Hz, 1 H, CHMe$_2$), 5.91 (bs, 1 H, NH).

$^{13}$C NMR (CDCl$_3$, 75.5 MHz, 300 K): δ (in ppm)=17.4 (MeC), 24.4 (CHMe$_2$), 43.9 (NCHMe$_2$), 46.5 (NMe$_2$), 157.8 (CMe).

Preparation of the Metal Complexes of the Invention

In the examples below, Examples 1 to 16 describe complexes with the ligand bdma and H-bdma, Examples 17 and 18 describe complexes with the ligand mdma and Example 19 describes a complex with the ligand dama. Example 20 reports a complex with the ligand bdmf and example 21 describes a Ga-complex with the dapa ligand.

Example 1

Preparation of [Li-bdma]

5.00 g (29.88 mmol, 1.00 equivalent) of LiHMDS are dissolved in 40 ml of hexane. Added thereto at room temperature are 5.17 g (35.85 mmol, 1.20 equivalents) of Hbdma, the solution warming slightly and a phase separation (liquid/liquid) being observed. The reaction mixture is stirred overnight, during which a colourless solid forms. The supernatant solution is decanted and the solid is washed with twice 20 ml of hexane. Drying under a fine vacuum gives 4.22 g (28.09 mmol, 94%) of a colourless solid. Yield: 2.57 g (17.1 mmol, 94%).

$^1$H NMR (C$_6$D$_6$, 300.1 MHz, 300 K): δ (in ppm)=2.24 (s, 3 H, CCH$_3$), 2.47 (s, 12 H, N(CH$_3$)$_2$), 2.53 (s, 12 H, N(CH$_3$)$_2$).

$^{13}$C NMR (C$_6$D$_6$, 75.5 MHz, 300 K): δ (in ppm)=17.3 (MeC), 48.2 (NMe$_2$), 50.3 (NMe$_2$), 170.1 (MeC).

Elemental analysis: C$_6$H$_{15}$LiN$_4$: calculated: C, 47.99%, H, 10.07%, N, 37.31%. found: C, 47.46%, H, 9.68%, N, 36.35%.

IR: 2969 (w), 2934 (w), 2840 (w), 2803 (w), 2758 (w), 1521 (vs), 1430 (m), 1395 (m), 1171 (m), 1058 (m), 1008 (m), 954 (s), 658 (s), 561 (s), 423 (m).

Example 2

Preparation of [K-bdma]

5.00 g (25.06 mmol, 1.00 equivalent) of KHMDS are dissolved in 50 ml of toluene and the solution is admixed dropwise at room temperature with 4.01 g (27.80 mmol, 1.11 equivalents) of Hbdma. During the addition, a colourless solid begins to precipitate, and after overnight stirring at room temperature is filtered off on a G4 frit. Washing with a few portions of hexane and drying under a fine vacuum give 4.16 g (22.80 mmol, 91%) of a colourless solid.

Elemental analysis: C$_6$H$_{15}$KN$_4$: calculated: C, 39.53%, H, 8.29%, N, 30.73%. found: C, 39.25%, H, 8.25%, N, 30.22%.

IR: 2962 (w), 2924 (w), 2829 (w), 2792 (m), 2748 (m), 1511 (vs), 1426 (m), 1371 (m), 1159 (m), 947 (s), 631 (m), 455 (m).

Example 3

Preparation of [Ga(bdma)H$_2$]

1.95 g (245.28 mmol, 13.10 equivalents) of LiH are suspended in 30 ml of Et$_2$O and the grey suspension is cooled to −78° C. This suspension is admixed dropwise with a solution, cooled to −78° C., of 2.70 g (15.33 mmol, 0.82 equivalent) of GaCl$_3$ in 15 ml of Et$_2$O and the resulting suspension is warmed slowly to room temperature overnight in an ice bath, with stirring. The suspension is subsequently filtered through a G4 frit (without Celite) into a flask, which has been cooled to −78° C. beforehand, and is admixed dropwise at −78° C. with a solution, cooled to −78° C., of 0.83 g (4.71 mmol, 0.25 equivalent) of GaCl₃ in 10 ml of Et₂O. The suspension is slowly warmed to about −25° C., then filtered through a G4 frit (without Celite) into a dropping funnel, which has been cooled to −78° C. beforehand, and the clear solution is added dropwise at −78° C. to a solution, cooled to −78° C., of 2.70 g (18.70 mmol, 1.00 equivalent) of Hbdma in 20 ml of Et₂O. The suspension which forms is warmed slowly to room temperature overnight with stirring; during this time, the colourless solid formed dissolves slowly with evolution of gas (H₂). The colourless solution obtained is filtered over Celite and the solvent is removed under a fine vacuum at 0° C. The colourless liquid which remains is distilled at 0.5 mbar and 50° C. to give 2.10 g (9.81 mmol, 52%) of the product as a low-viscosity liquid.

$^1$H NMR (C₆D₆, 300.1 MHz, 300 K): δ (in ppm)=2.00 (s, 3 H, MeC), 2.30 (s, 12 H, NMe₂), 5.30 (bs, 2 H, GaH₂).

$^{13}$C NMR (C₆D₆, 75.5 MHz, 300 K): δ (in ppm)=15.6 (MeC), 49.7 (NMeMe), 51.0 (NMeMe), 167.2 (MeC).

HR-EI-MS: calculated for C₆H₁₇GaN₄: 214.0709 m/z. found: 214.0715 m/z.

IR: 2978 (m), 2944 (m), 2850 (m), 2811 (m), 2767 (m), 1866 (s), 1550 (vs), 1405 (vs), 957 (s), 744 (vs), 651 (vs).

Due to the low proportions of carbon it is possible, when using this precursor for the deposition of GaN layers in CVD processes, to minimize the incorporation of C impurities (in the form of carbides, for example).

Example 4

Preparation of [Al(bdma)Me₂]

1 ml of an AlMe₃ solution in toluene (1.43 mol/l; 1.43 mmol, 1.00 equivalent) is introduced into 30 ml of hexane and the solution is cooled to −78° C. and admixed slowly with 222 mg (1.54 mmol, 1.08 equivalents) of Hbdma. Following the addition, the cooling bath is removed and the reaction mixture stirred at room temperature for twelve hours. Removal of the solvent and sublimation of the solid which remains under a fine vacuum give 246 mg (1.23 mmol, 86%) of a colourless solid. Melting point: 41° C.

$^1$H NMR (C₆D₆, 300.1 MHz, 300 K): δ (in ppm)=−0.41 (s, 6 H, AlMe₂), 2.01 (s, 3 H, MeC), 2.17 (s, 6 H, NMe₂), 2.36 (s, 6 H, NMe₂).

$^{13}$C NMR (C₆D₆, 75.5 MHz, 300 K): δ (in ppm)=−8.7 (AlMe₂), 15.9 (MeC), 48.1 (NMe₂), 49.5 (NMe₂), 168.7 (MeC).

HR-EI-MS: calc. for C₈H₂₁N₄Al: 200.1582 m/z. found: 200.1587 m/z.

Elemental analysis: C₈H₂₁AlN₄: calculated: C, 47.98%, H, 10.57%, N, 27.98%. found: C, 47.69%, H, 10.57%, N, 27.68%.

IR: 2980 (w), 2944 (w), 2885 (w), 2850 (w), 2814 (w), 2772 (w), 1549 (m), 1403 (m), 1190 (m), 952 (m), 663 (s), 630 (m), 592 (m), 557 (m).

Example 5

Preparation of [Ga(bdma)(NMe₂)₂]

A suspension of 1.15 g (22.55 mmol, 3.00 equivalents) of LiNMe₂ in 20 ml of Et₂O is admixed at −78° C. with a solution of 1.32 g (7.50 mmol, 1.00 equivalent) of GaCl₃ in 10 ml of Et₂O. After the end of the addition, the cooling bath is removed and the colourless suspension is stirred at room temperature for 30 minutes. Then 1.08 g (7.50 mmol, 1.00 equivalent) of Hbdma in solution in 10 ml of Et₂O are added at room temperature. The suspension is stirred at room temperature overnight and then centrifuged. The clear centrifuge product is freed from the solvent under a fine vacuum and recondensed at 1 mbar/110° C. This gives 1.22 g (4.05 mmol, 54% based on GaCl₃) of a colourless solid of low melting point.

$^1$H NMR (C₆D₆, 300.1 MHz, 300 K): δ (in ppm)=2.07 (s, 3 H, MeC), 2.27 (s, 6 H, NNMe₂), 2.35 (s, 6 H, NNMe₂), 2.81 (s, 12 H, Ga(NMe₂)₂).

$^{13}$C NMR (C₆D₆, 75.5 MHz, 300 K): δ (in ppm)=17.0 (MeC), 43.2 (Ga(NMe₂)₂), 48.5 (NNMe₂), 48.9 (NNMe₂), 168.3 (MeC).

HR-EI-MS: calculated for C₁₀H₂₇GaN₆: 300.1553 m/z. found: 300.1545 m/z.

IR: 2944 (w), 2853 (w), 2810 (m), 2762 (s), 1552 (s), 1399 (s), 1178 (s), 965 (vs), 952 (vs), 631 (s), 545 (s).

Example 6

Preparation of [Ga(bdma)Cl₂]

205 mg (1.16 mmol, 1.00 equivalent) of GaCl₃ are weighed out into a Schlenk flask and then about 10 ml of Et₂O are condensed in at −196° C. After the mixture has warmed to room temperature, a suspension of 174 mg (1.16 mmol, 1.00 equivalent) of Libdma in Et₂O is slowly added. The colourless suspension is subsequently stirred overnight, the solvent is removed under a fine vacuum and the product is obtained from the solid which remains by sublimation. This yields 309 mg (1.09 mmol, 94%) of a colourless solid.

Example 7

Preparation of [In(bdma)Me₂]

200 mg (1.25 mmol, 1.00 equivalent) of InMe₃ are dissolved in 10 ml of toluene at room temperature and the solution is admixed at room temperature with 180 mg (1.25 mmol, 1.00 equivalent) of Hbdma. Following initial evolution of gas and stirring of the solution overnight at room temperature, the solvent is removed under a fine vacuum. The solid which remains is sublimed under a fine vacuum, to yield 292 mg (1.01 mmol, 81%) of a colourless solid. Melting point: 47° C.

$^1$H NMR (C₆D₆, 300.1 MHz, 300 K): δ (in ppm)=−0.02 (s, 6 H, InMe₂), 2.14 (s, 3 H, MeC), 2.20 (bs, 12H, NMe₂).

$^{13}$C NMR (C₆D₆, 75.5 MHz, 300 K): δ (in ppm)=−6.4 (InMe₂), 17.4 (MeC), 49.4 (NMe₂), 50.8 (NMe₂), 167.8 (MeC).

HR-EI-MS: calc. for C₈H₂₁N₄In: 288.0805 m/z. found: 288.0811 m/z.

Elemental analysis: C₈H₂₁InN₄: calculated: C, 33.35%, H, 7.35%, N, 19.45%. found: C, 33.20%, H, 7.24%, N, 19.47%.

IR: 2979 (w), 2939 (m), 2880 (w), 2841 (w), 2802 (w), 2755 (m), 1537 (s), 1392 (s), 949 (s), 507 (vs).

This complex is highly volatile and sublimes without decomposition at 0.1 mbar and 80° C. FIG. 1 shows the X-ray structure analysis of the compound.

Example 8

Preparation of [Ti(bdma)(NMe₂)₃]

221 mg (0.98 mmol, 1.00 equivalent) of Ti(NMe₂)₄ are dissolved in 5 ml of toluene and this solution is admixed at 0° C. with 284 mg (1.97 mmol, 2.00 equivalents) of Hbdma. The clear yellow solution is subsequently stirred at 60° C. overnight and, after cooling to room temperature and removal of the solvent under a fine vacuum, 294 mg (0.91 mmol, 93%) of a bright yellow oil are obtained.

$^1$H NMR (C$_6$D$_6$, 300.1 MHz, 300 K): δ (in ppm)=2.25 (s, 3 H, MeC), 2.74 (bs, 12 H, N-NMe$_2$), 3.12 (s, 18 H, Ti—NMe$_2$).

$^{13}$C NMR (C$_6$D$_6$, 75.5 MHz, 300 K): δ (in ppm)=15.0 (MeC), 46.0 (Ti—NMe$_2$), 47.3 (bs, N-NMe$_2$).

$^1$H NMR (C$_6$D$_5$CD$_3$, 500,1 MHz, 232 K): δ (in ppm)=2.38 (s, 3 H, MeC), 2.57 (s, 6 H, N-NMe$_2$), 2.97 (s, 6 H, N-NMe$_2$), 3.12 (s, 18 H, Ti—NMe$_2$).

$^{13}$C NMR (C$_6$D$_5$CD$_3$, 125.8 MHz, 232 K): δ (in ppm)=15.1 (MeC), 45.4 (N-NMe$_2$), 46.0 (Ti—NMe$_2$), 48.7 (N-NMe$_2$), 163.1 (MeC).

HR-EI-MS: calc. for C$_{12}$H$_{33}$N$_7$Ti: 323.2278 m/z. found: 323.2272 m/z.

IR: 2965 (w), 2939 (w), 2839 (m), 2807 (m), 2761 (m), 1580 (m), 1359 (m), 1316 (s), 1242 (m), 1052 (m), 944 (vs), 583 (s), 559 (s), 448 (m).

Example 9

Preparation of [Hf(bdma)$_2$Cl$_2$]

261 mg (0.81 mmol, 1.00 equivalent) of HfCl$_4$ and 245 mg (1.63 mmol, 2.00 equivalents) of Libdma are introduced together in a Schlenk flask and admixed at room temperature with 30 ml of THF. The resulting suspension is heated at boiling temperature for four hours and, after cooling to room temperature, the solvent is removed under a fine vacuum. The solid which remains is admixed with 30 ml of dichloromethane and stirred overnight. The colourless suspension is then admixed with 30 ml of hexane and filtered through a G4 frit. Drying of the solid under a fine vacuum gives 301 mg (0.56 mmol, 69%) of a colourless solid.

$^1$H NMR (C$_6$D$_6$, 300.1 MHz, 300 K): δ (in ppm)=1.67 (s, 6 H, MeC), 2.12 (s, 6 H, NMeMe)), 2.51 (s, 6 H, NMeMe), 2.87 (s, 6 H, NMeMe), 3.19 (s, 6 H, NMeMe).

$^{13}$C NMR (C$_6$D$_6$, 75.5 MHz, 300 K): δ (in ppm)=16.0 (MeC), 44.4 (NMeMe), 45.7 (NMeMe), 51.7 (NMeMe), 52.0 (NMeMe), 163.9 (MeC).

HR-EI-MS: calc. for C$_{12}$H$_{30}$Cl$_2$HfN$_8$: 536.1436 m/z. found: 536.1442 m/z.

IR: 2957 (w), 2912 (m), 2867 (w), 1574 (s), 1380 (s), 1342 (vs), 939 (vs), 854 (s), 823 (s), 618 (s), 504 (s), 441 (s), 408 (s).

Example 10

Preparation of [Ta(bdma)Cl$_4$]

2.27 g (3.17 mmol, 1.00 equivalent) of [TaCl$_5$]$_2$ are suspended in 50 ml of toluene, and dissolved with heating, and the solution is cooled slowly to room temperature, with stirring. In a separate Schlenk flask, 1.05 g (7.01 mmol, 1.10 equivalents) of Libdma are slurried in 5 ml of toluene and admixed with 2 ml (1.70 g, 15.65 mmol, 2.50 equivalents) of TMSCl. The resulting suspension is heated at boiling heat briefly (about 5 minutes), cooled and added dropwise to the TaCl$_5$ suspension, which is cooled at 0° C., and the blood-orange suspension which forms is heated to 70° C. After twelve hours, the suspension is filtered through Celite, and the product begins to crystallize. After the orange solution has been concentrated to half its volume and cooled at −23° C., 1.84 g (3.95 mmol, 62%) of a yellow solid are obtained.

$^1$H NMR (CDCl$_3$, 300.1 MHz, 300 K): δ (in ppm)=2.33 (s, 3 H, MeC), 3.25 (s, 6 H, NMe$_2$), 3.50 (s, 6 H, NMe$_2$).

$^{13}$C NMR (CDCl$_3$, 75.5 MHz, 300 K): δ (in ppm)=13.6 (MeC), 48.9 (NMe$_2$), 54.2 (NMe$_2$), 160.1 (MeC).

$^1$H NMR (C$_6$D$_6$, 300.1 MHz, 300 K): δ (in ppm)=1.25 (s, 3 H, MeC), 2.62 (s, 6 H, NMe$_2$), 3.02 (s, 6 H, NMe$_2$).

$^{13}$C NMR (C$_6$D$_6$, 75.5 MHz, 300 K): δ (in ppm)=12.7 (MeC), 47.9 (NMe$_2$), 53.9 (NMe$_2$), 160.1 (MeC).

HR-EI-MS: calc. for C$_6$H$_{15}$Cl$_4$N$_4$Ta: 463.9531 m/z. found: 463.9523 m/z.

Elemental analysis: C$_6$H$_{15}$Cl$_4$N$_4$Ta: calculated: C, 15.47%, H, 3.24%, N, 12.02%. found: C, 15.38%, H, 3.16%, N, 12.38%.

IR: 2936 (w), 1607 (m), 1453 (m), 1379 (vs), 1341 (vs), 953 (s), 851 (s), 606 (s), 520 (m), 444 (m).

Example 11

Preparation of [Si(bdma)Cl$_3$]

752 mg (4.43 mmol, 1.00 equivalent) of SiCl$_4$ are introduced into 20 ml of dichloromethane and admixed at room temperature with a mixture of 460 mg (4.54 mmol, 1.02 equivalents) of triethylamine and 650 mg (4.51 mmol, 1.02 equivalents) of Hbdma. The clear solution is stirred at room temperature for three hours and then admixed with 20 ml of hexane. The resulting suspension is filtered through Celite and subsequently the solvent of the clear solution is removed under a fine vacuum. The solid which remains is dissolved in 20 ml of hot hexane (about 40° C.) and again filtered through Celite. Removal of the solvent under a fine vacuum yields 350 mg (1.27 mmol, 28%) of a colourless solid.

$^1$H NMR (C$_6$D$_6$, 300.1 MHz, 300 K): δ (in ppm)=1.58 (s, 3 H, MeC), 2.54 (s, 12 H, NMe$_2$).

$^{13}$C NMR (C$_6$D$_6$, 75.5 MHz, 300 K): δ (in ppm)=8.9 (MeC), 46.4 (NMe$_2$), 175.6 (MeC).

HR-EI-MS: calc. for C$_6$H$_{15}$Cl$_3$N$_4$Si: 276.0132 m/z. found: 276.0128 m/z.

Elemental analysis: C$_6$H$_{15}$Cl$_3$N$_4$Si: calculated: C, 25.95%, H, 5.45%, N, 20.18%. found: C, 26.02%, H, 5.62%, N, 20.87%.

IR: 2989 (w), 2957 (w), 2869 (w), 2835 (w), 2789 (w), 1607 (m), 1442 (m), 1388 (m), 1023 (m), 965 (m), 928 (m), 878 (m), 845 (m), 609 (s), 568 (s), 536 (vs), 446 (s), 419 (vs).

The compound is a colourless, highly volatile solid which sublimes without decomposition at 0.1 mbar and 80° C. It can be used as a precursor for producing silicon nitride layers by means of CVD processes.

Example 12

Preparation of [Ta(N$^t$Bu)Cl$_3$(H-bdma)]

873 mg (1.67 mmol, 1.00 equivalent) of [Ta(N$^t$Bu)Cl$_3$py$_2$] are suspended in 50 ml of toluene. The yellow suspension is admixed at room temperature with 483 mg (3.35 mmol, 2.00 equivalents) of Hbdma. After a short time a pale yellow, clear solution is formed and after overnight stirring the solvent is removed under a fine vacuum. The pale yellow residue is dissolved in 25 ml of dichloromethane and the colourless solution is clarified using a syringe filter. Following concentration to a volume of approximately 10 ml the solution is admixed with 50 ml of pentane, with stirring, and the colourless solid which precipitates is removed by centrifugation and dried under a fine vacuum. This gives 713 mg (1.42 mmol, 85%) of a colourless, finely crystalline solid.

$^1$H NMR (C$_6$D$_6$, 300.1 MHz, 300K): δ (in ppm)=1.45 (s, 3 H, MeC), 1.62 (s, 9 H, N$^t$Bu), 2.67 (s, 6 H, NMe$_2$), 2.96 (s, 6 H, NMe$_2$), 5.84 (s, 1 H, NH).

$^{13}$C NMR (C$_6$D$_6$, 75.5 MHz, 300 K): δ (in ppm)=15.6 (MeC), 32.4 (NCMe$_3$), 46.8 (NMe$_2$), 52.6 (NMe$_2$), 66.7 (NCMe$_3$), 167.7 (MeC).

HR-EI-MS: calc. for C$_{10}$H$_{24}$Cl$_2$N$_5$Ta: 465.0889 m/z. found: 465.0885 m/z.

Elemental analysis: C$_{10}$H$_{26}$Cl$_3$N$_5$Ta: calculated: C, 23.89%, H, 5.01%, N, 13.93%. found: C, 23.63%, H, 5.36%, N, 13.76%.

IR: 3241 (m), 3093 (w), 2973 (w), 2920 (w), 2885 (w), 1575 (s), 1442 (m), 1263 (vs), 874 (s), 552 (m), 498 (m).

Example 13

Preparation of [V(bdma)$_3$]

359 mg (0.96 mmol, 1.00 equivalent) of [VCl$_3$(THF)$_3$] are suspended in 5 ml of THF and the violet suspension is admixed dropwise with a solution of 525 mg (2.88 mmol, 3.00 equivalents) of Kbdma in 5 ml of THF. After twelve hours of stirring at room temperature, the precipitated KCl is removed by centrifugation, the supernatant violet solution is decanted off, and the solvent is removed under a fine vacuum. The solid which remains is admixed with 40 ml of hexane and the resultant suspension is filtered through Celite. Concentration of the solvent volume to approximately 10 ml and storage overnight at −23° C. give 354 mg (2.22 mmol, 77%) of an intense-violet crystalline solid.

HR-EI-MS: calc. for C$_{18}$H$_{45}$N$_{12}$V: 480.3330 m/z. found: 480.3336 m/z Elemental analysis: C$_{18}$H$_{45}$N$_{12}$V: calculated: C, 44.99%, H, 9.44%, N, 34.98%. found: C, 44.56%, H, 9.32%, N, 34.57%.

IR: 2973 (w), 2940 (m), 2852 (m), 2816 (m), 2777 (w), 1576 (m), 1368 (vs), 1314 (vs), 1016 (m), 942 (s), 635 (m), 534 (m), 454 (w).

Example 14

Preparation of [Ni(bdma)$_2$]

330 mg (1.50 mmol, 1.00 equivalent) of [NiCl$_2$(DME)] are suspended in 20 ml of toluene and admixed with a suspension of 451 mg (3.00 mmol, 2.00 equivalents) of Libdma in 50 ml of toluene. The suspension, which slowly takes on a brown coloration, is heated at 60° C. for four hours. After cooling to room temperature the solvent is removed under a fine vacuum, the solid which remains is admixed with 80 ml of hexane, and the suspension which forms is stirred at room temperature for 30 minutes. The red-brown suspension is then filtered through Celite and the filter cake is extracted with small amounts of hexane until the filtrate is completely colourless. Removal of the solvent under a fine vacuum and sublimation of the residue yields 428 mg (1.24 mmol, 83%) of the product as a green solid.

$^1$H NMR (C$_6$D$_6$, 300.1 MHz, 300 K): δ (in ppm)=0.08 (bs, 10 H), 4.48 (bs, 20 H).

$^1$H NMR (C$_6$D$_5$CD$_3$, 500.1 MHz, 223 K): δ (in ppm)=1.87 (s, 6 H, MeC), 2.41 (s, 12 H, NMe$_2$), 2.70 (s, 12 H, NMe$_2$).

$^{13}$C NMR (C$_6$D$_5$CD$_3$, 125.7 MHz, 223 K): δ (in ppm)=15.7 (MeC), 46.2 (NMe$_2$), 49.3 (NMe$_2$), 170.0 (MeC).

HR-EI-MS: calc. for C$_{12}$H$_{30}$N$_8$Ni: 344.1947 m/z. found: 344, 1964 m/z.

Elemental analysis: C$_{12}$H$_{30}$N$_8$Ni: calculated: C, 41.76%, H, 8.76%, N, 32.47%. found: C, 41.24%, H, 8.33%, N, 32.10%.

IR: 3039 (w), 2980 (w), 2904 (m), 2848 (m), 2772 (m), 1566 (vs), 1445 (m), 1380 (vs), 1340 (vs), 1220 (m), 1173 (m), 1094 (m), 950 (vs), 904 (s), 866 (m), 838 (m), 616 (s), 570 (s), 535 (m), 455 (m), 431 (s).

Example 15

Preparation of [Pd(bdma)$_2$]

90 mg (0.35 mmol, 1.00 eq) of [PdCl$_2$(MeCN)$_2$] are dissolved in 10 ml of THF and the solution is cooled to 0° C. At this temperature a solution of 133 mg (0.73 mmol, 2.00 eq) of Kbdma in 10 ml of THF is added dropwise. The reaction mixture, warmed to room temperature, is stirred for 18 hours and then centrifuged. From the clear solution the THF is removed under vacuum, giving the product as a yellow powder. 103 mg (0.26 mmol; 76%) of [Pd(bdma)$_2$] are recovered.

$^1$H NMR (C$_6$D$_6$, 300.1 MHz, 300 K): δ (in ppm)=1.98 (s, 6 H, CCH$_3$), 2.54 (s, 12 H, NNCH$_3$), 2.82 (s, 12 H, PdNCH$_3$).

$^{13}$C NMR (C$_6$D$_6$, 75.5 MHz, 300 K): δ (in ppm)=15.0 (CCH$_3$), 45.8 (PdNCH$_3$), 51.9 (NNCH$_3$), 169.9 (NCCH$_3$).

HR-EI-MS: calc. for C$_{12}$H$_{30}$N$_8$Pd: 392.1628 m/z. found: 392.1621 m/z.

Elemental analysis: C$_{12}$H$_{30}$N$_8$Pd: calculated: C, 36.68%, H, 7.69%, N, 28.52%. found: C, 37.04%, H, 7.58%, N, 23.25%.

Example 16

Preparation of [Al(bdma)H(μ-H)]$_2$ 107 mg (2.82 mmol, 0.75 equivalent) of LiAlH$_4$ are dissolved in 5 ml of Et$_2$O and this solution is added to a solution, cooled to −78° C., of 126 mg (0.94 mmol, 0.25 equivalents) of AlCl$_3$ in 5 ml of Et$_2$O. The solution is stirred until the cooling bath has reached a temperature of −40° C., with a marked clouding being observed (LiCl). The suspension is subsequently cooled to −78° C. again and admixed with 543 mg (3.76 mmol, 1.00 equivalent) of Hbdma in 10 ml of Et$_2$O. Following removal of the cooling bath, the mixture is stirred at room temperature overnight. The colourless suspension is then filtered through Celite, the filter cake is extracted with twice 5 ml of Et$_2$O, the solvent is removed under a fine vacuum and the colourless solid which remains is sublimed. This gives 595 mg (3.46 mmol, 92%) of the product as a finely crystalline colourless solid.

$^1$H NMR (C$_6$D$_6$, 300.1 MHz, 300 K): δ (in ppm)=1.99 (s, 3 H, MeC), 2.26 (s, 6 H, NMe$_2$), 2.40 (s, 6 H, NMe$_2$), 4.54 (s, 2 H, AlH$_2$).

$^{13}$C NMR (C$_6$D$_6$, 75.5 MHz, 300 K): δ (in ppm)=15.7 (MeC), 49.2 (NMe$_2$), 49.7 (NMe$_2$), 169.2 (MeC).

HR-EI-MS: calc. for C$_6$H$_{17}$AlN$_4$: 172.1269 m/z. found: 172.1270 m/z.

Elemental analysis: C$_6$H$_{17}$AlN$_4$: calculated: C, 41.85%, H, 9.95%, N, 32.53%. found: C, 41.53%, H, 9.56%, N, 32.10%.

IR: 2975 (w), 2934 (w), 2855 (w), 2818 (w), 2777 (w), 1831 (s), 1565 (s), 1390 (vs), 1343 (s), 950 (s), 840 (s), 679 (s), 636 (s), 553 (s), 524 (s).

Example 17

Preparation of [Al(mdma)$_2$H]

43 mg (1.13 mmol, 1.00 equivalent) of LiAlH$_4$ are dissolved in 10 ml of Et$_2$O and admixed at −78° C. in portions with 108 mg (1.13 mmol, 1.00 equivalent) of Me$_3$N*HCl. The colourless suspension is warmed slowly to −20° C. with stirring, and is stirred at this temperature until the evolution of gas (H$_2$) is at an end. The colourless suspension is then cooled to −78° C. again and a solution of 229 mg (2.26 mmol, 2.00 equivalents) of Hmdma in 10 ml of Et$_2$O is slowly added. The suspension obtained is stirred overnight, accompanied by slow warming to room temperature. The colourless suspension is then freed from the solvent under a fine vacuum; the solid which remains is stirred with 20 ml of benzene at room temperature for two hours and the reaction mixture is subsequently filtered through Celite. Following concentration of the solvent volume to approximately 7 ml, overlayering with 14 ml of hexane and removal of the solvent mixture, drying of the solid which remains under a fine vacuum produces 90 mg (0.39 mmol, 34%) of a crystalline solid.

$^1$H NMR(C$_6$D$_6$, 300.1 MHz, 300 K): δ (in ppm)=1.70 (s, 6 H, MeC), 2.22 (s, 6 H, NMeMe), 2.51 (s, 6 H, NMeMe), 3.36 (bs, 2 H, NH).

$^{13}$C NMR (C$_6$D$_6$, 75.5 MHz, 300 K): δ (in ppm)=20.4 (MeC), 47.2 (NMeMe), 50.0 (NMeMe), 166.1 (MeC).

Elemental analysis: C$_8$H$_{21}$AlN$_6$: calculated: C, 42.09%, H, 9.27%, N, 36.82%. found: C, 41.79%, H, 9.44%, N, 36.79%.

IR: 3338 (m), 3007 (w), 2987 (w), 2973 (m), 2922 (m), 1773 (m), 1584 (s), 1424 (vs), 1408 (vs), 977 (s), 620 (m), 584 (vs), 428 (vs).

Example 18

Preparation of [Ga(mdma)$_2$H]

336 mg (1.91 mmol, 1.25 equivalents) of GaCl$_3$ are dissolved in 10 ml of Et$_2$O and this solution is admixed dropwise at −78° C. to a suspension of 236 mg (29.68 mmol, 19.43 equivalents) of LiH. The suspension is slowly warmed to room temperature overnight, with stirring, and then filtered (without Celite) through a G4 frit into a flask, which has been cooled to −78° C. beforehand, and the filter cake which remains is extracted with twice 5 ml of Et$_2$O, cooled to −78° C. beforehand. The clear LiGaH$_4$ solution is admixed at −78° C. in portions with 144 mg (1.51 mmol, 1.00 equivalent) of Me$_3$N*HCl, and the suspension obtained is stirred with slow warming until the evolution of gas (H$_2$) is at an end. Subsequently it is cooled again to −78° C. and a solution of 306 mg (3.02 mmol, 2.00 equivalents) of Hmdma in 15 ml of Et$_2$O is slowly added. After the end of the addition, the cooling bath is removed and the colourless suspension is stirred at room temperature overnight. The colourless suspension is subsequently dried under a fine vacuum and the solid which remains is admixed with 25 ml of benzene. The suspension is filtered through Celite, the filter cake is extracted with three times 5 ml of benzene, and the solvent is removed under a fine vacuum. The solid which remains is slurried with 5 ml of hexane and, following decanting and drying of the solid which remains, 170 mg (0.63 mmol, 42%) of a fine, colourless solid are obtained.

$^1$H NMR (C$_6$D$_6$, 300.1 MHz, 300 K): δ (in ppm)=1.75 (s, 6 H, MeC), 2.30 (s, 12H, NMe$_2$), 3.58 (bs, 2 H, NH), 4.97 (bs, 1 H, GaH).

$^{13}$C NMR (C$_6$D$_6$, 75.5 MHz, 300 K): δ (in ppm)=20.7 (MeC), 48.3 (NMe$_2$), 164.7 (MeC).

HR-EI-MS: calc. for C$_8$H$_{21}$GaN$_6$: 270.1084 m/z. found: 270.1083 m/z.

IR: 3328 (m), 2961 (m), 2911 (m), 2879 (m), 1867 (s), 1580 (vs), 1413 (vs), 985 (s), 587 (s), 540 (s), 503 (s).

Example 19

Preparation of [Ga(dama)Me$_2$]

1.34 g (11.65 mmol, 1.00 equivalent) of GaMe$_3$ are condensed at 77 K into a Schlenk flask and admixed with 10 ml of hexane. Following warming to −78° C., 1.33 g (11.56 mmol, 0.99 equivalent) of Hdama are added. The colourless solid which forms at the start slowly dissolves in the course of warming to room temperature with evolution of gas. The solvent is distilled off under atmospheric pressure, and the oily liquid which remains is distilled under reduced pressure (15 mbar, 73° C.). This gives 1.40 g (6.54 mmol, 56%) of a colourless liquid.

$^1$H NMR (C$_6$D$_6$, 300.1 MHz, 300 K): δ (in ppm)=−0.21 (s, 6 H, GaMe$_2$), 1.68 (s, 3H, MeC), 2.21 (s, 6 H, NMe$_2$), 2.57 (s, 3 H, NMe).

$^{13}$C NMR (C$_6$D$_6$, 75.5 MHz, 300 K): δ (in ppm)=−8.9 (GaMe$_2$), 15.5 (MeC), 32.0 (NMe), 49.1 (NMe$_2$), 166.1 (MeC).

HR-EI-MS: calc. for C$_7$H$_{18}$GaN$_3$: 213.0757 m/z. found: 213.0766 m/z.

IR: 3003 (w), 2927 (m), 2888 (m), 2810 (w), 1552 (vs), 1422 (s), 1398 (s), 1192 (m), 942 (m), 569 (s), 536 (s).

Example 20

Preparation of [Pd(bdmf)$_2$]

270 mg (1.35 mmol, 4.00 equivalents) of KHMDS are dissolved in 5 mL of toluene and the solution is admixed dropwise at room temperature with 118 mg (0.91 mmol, 2.7 equivalents) of Hbdmf. The reaction mixture is stirred for 1 h, the colorless precipitate Kbdmf is separated and washed with 3 mL hexane and dried in vacuo. 130 mg Kbdmf (0.77 mmol, 2.3 equivalents) are dissolved in 3 mL THF, this solution is slowly added to 88 mg [PdCl$_2$(MeCN)$_2$] (0.34 mmol, 1.00 equivalent) dissolved in 3 mL THF and stirred for 12 h at 25° C. The brownish precipitate of KCl is separated and volatiles are removed from the orange solution. The yellow-orange solid is washed with hexane and recrystallized from toluene to give 51 mg (0.31 mmol, 41%) of single crystalline product, which is analyzed by single crystal XRD analysis.

$^1$H NMR (C$_6$D$_6$, 300.1 MHz, 300 K): δ (in ppm)=3.52 (s, 2 H CH) 2.65 (s, 12 H, PdNMe$_2$), 2.47 (m, 12H, NNMe$_2$).

$^{13}$C NMR (C$_6$D$_6$, 75.5 MHz, 300 K): δ (in ppm)=157.2 (CH), 52.7 (PdNMe$_2$), 47.3 (NNMe$_2$).

HR-MS: calc. for C$_{10}$H$_{27}$N$_8$Pd, [M+H]$^+$: 365.1389 m/z. found: 365.1389 m/z.

IR: 2962 (w), 1569 (w), 1447 (m), 1259 (m), 1078 (m), 1012 (s), 950 (w), 865 (w), 792 (s), 702 (w), 596 (w), 569 (w), 533 (w), 470 (m), 435 (m).

Example 21

Preparation of [Ga(dapa)Me$_2$]

A solution of 350 mg (1.99 mmol, 1.00 equivalent) of GaCl$_3$ in 20 mL of diethyl ether is admixed with 4.0 mL of a MeLi-solution (solvent: diethyl ether; c=1.555 mol/L, 6.22 mmol, 3.10 equivalents). After the end of the addition, the suspension is stirred for two hours at room temperature. After cooling to 0° C., 290 mg (2.02 mmol, 1.02 equivalents) of Hdapa is added dropwise. After the end of the addition, the cooling bath is removed and the colourless suspension is stirred at room temperature for three days (72 h). The suspension is filtrated over a bed of Celite™ and the clear solution is stripped in vacuo. After sublimation of the remaining colourless solid, 368 mg (1.52 mmol, 76%) of the product as colourless crystals are obtained.

$^1$H NMR (C$_6$D$_6$, 300.1 MHz, 300 K): δ (in ppm)=−0.10 (s, 6 H, GaMe$_2$), 1.03 (d, $^3J_{HH}$=6.4 Hz, 6 H, CHMe$_2$), 1.77 (s, 3 H, CMe), 2.21 (s, 6 H, NMe$_2$), 3.38 (sept, 1H, $^3J_{HH}$=6.4 Hz, CHMe$_2$).

$^{13}$C NMR (C$_6$D$_6$, 75.5 MHz, 300 K): δ (in ppm)=−6.0 (GaMe$_2$), 16.1 (CMe), 25.9 (CHMe$_2$), 47.1 (CHMe$_2$), 48.9 (NMe$_2$), 164.0 (CMe).

HR-EI-MS: calculated for C$_9$H$_{22}$GaN$_3$: 241.1070 m/z. found: 241.1059 m/z.

IR: 3007 (w), 2961 (m), 2927 (m), 1542 (vs), 1471 (m), 1449 (vs), 1424 (s), 1400 (m), 1193 (vs), 1004 (m), 560 (vs), 538 (vs).

Elemental analysis: C$_9$H$_{22}$GaN$_3$: calculated: C, 44.67%, H, 9.16%, N, 17.36%. found: C, 43.82%, H, 9.70%, N, 17.68%.

Example 22

Implementation of CVD Experiments

Layers with different, reproducible amounts of metal and nitrogen are deposited on a commercial Aixtron AIX-200 reactor with hydrogen, ammonia or nitrogen as carrier gas. During the operation, the pressure in the reactor is set at a constant level of 50 to 150 mbar, preferably at 80 to 120 mbar and more preferred at 100 mbar. The gas flow rate is 400 to 700 sccm, preferably 500 to 600 sccm. The temperature in the stainless-steel bubbler, which contains the volatile metal complexes of the present invention, is kept constant at 30° C. in the case of the bdma-aluminum hydrides and bdma-gallium hydrides. The temperature of the reservoir container is regulated to 50 to 70° C. in the case of the bdma-metal alkyls and to 70 to 100° C. in the case of the bdma-metal amides and bdma-metal halides. Deposition takes place onto (100) oriented p-doped silicon wafers which are covered with a natural film of an SiO$_2$ surface or onto a (0001) surface of sapphire with substrate temperatures of between 200 and 800° C., preferably between 400 bis 600° C. With a constant, adjustable growth rate of 0.4 to 40.0 nm/min, amorphous polycrystalline or epitactic layers with thicknesses of 5 nm up to 15 µm can be obtained. An example is the deposition of high-quality layers of gallium nitride (GaN) on sapphire, from the precursor (bdma)GaH$_2$.

The thickness of the layers is detected using a scanning electron microscope (SEM); the elemental composition is analysed by means of energy-dispersive X-ray analysis (EDX); quality is assessed by means of photoluminescence spectroscopy (PL); and the crystalline phases are analysed using XRD methods.

The invention claimed is:

1. A metal complex having at least one N-aminoamidinate ligand, wherein the metal complex is constructed according to general formula 1

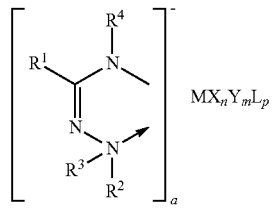

formula 1 wherein
M is a metal selected from groups 1 to 15 of the Periodic Table of the Elements (PTE), R$^1$ is hydrogen or a cyclic, linear or branched alkyl radical having up to 8 C atoms, or a substituted or unsubstituted aryl radical having up to 20 C atoms,
R$^2$ and R$^3$ independently of one another are hydrogen, CH$_3$ or C$_2$H$_5$,
R$^4$ is hydrogen, CH$_3$, NH$_2$, N(CH$_3$)$_2$ or N(C$_2$H$_5$)$_2$,
X is a monoanionic co-ligand selected from the group consisting of the hydride anion (H$^-$), the group of the halides, the group of the cyclic, linear or branched alkylide radicals having up to 8 C atoms, the group of substituted or unsubstituted arylide and heteroarylide radicals having up to 10 C atoms, the group of alkoxylato ligands, from the group of alkylthiolato or alkylselenato ligands, and the group of secondary amido ligands,
Y is a dianionic coligand selected from the group consisting of the oxo group [O]$^{2-}$ and the imido group [NR$^5$]$^{2-}$, where R$^5$ is a cyclic, branched or linear alkyl radical having up to 8 C atoms or is a substituted or unsubstituted aryl radical having up to 20 C atoms,
L is a neutral 2-electron donor ligand, wherein if M is scandium, L is not a pentamethylcyclopentadiene (Cp*) ligand,
a is an integer between 1 and 4, and
n, m, and p each independently of one another are 0, 1, 2, 3 or 4.

2. The metal complex according to claim 1, wherein
R$^1$ is CH$_3$, C$_2$H$_5$, C$_6$H$_5$, tolyl, 2,6-diisopropylphenyl or 2,4,6-trimethylphenyl (mesityl),
R$^2$ and R$^3$ independently of one another are hydrogen, CH$_3$ or C$_2$H$_5$,
R$^4$ is hydrogen, CH$_3$, NH$_2$, N(CH$_3$)$_2$ or N(C$_2$H$_5$)$_2$,
X is methylide (CH$_3$$^-$), ethylide (C$_2$H$_5$$^-$), isopropylide (iso-C$_3$H$_7$$^-$), tert-butylide (tert-C$_4$H$_9$$^-$), the phenylide anion (C$_6$H$_5$$^-$), the ortho-, meta-, or para-tolylide anion [C$_6$H$_4$(CH$_3$)]$^-$, the thiophen-2-ylide anion (C$_4$H$_3$S$^-$), methylato (MeO$^-$), ethylato (EtO$^-$), tert-butylato (tert-BuO$^-$), MeS$^-$, MeSe$^-$, (tert-Bu)S$^-$, (tert-Bu)Se$^-$, dimethylamido (NMe$_2$$^-$), diethylamido (NEt$_2$$^-$), methylethylamido (NMeEt$^-$) or N-pyrrolidido [NC$_4$H$_8$]$^-$, and
Y is the imido group [N$^t$Bu]$^{2-}$.

3. The metal complex according to claim 1, wherein the radical X is a hydride anion (H$^-$), chloride (Cl$^-$), bromide (Br$^-$), methylide (CH$_3$$^-$), ethylide (C$_2$H$_5$$^-$), dimethylamide (NMe$_2$$^-$) or diethylamide (NEt$_2$$^-$).

4. The metal complex according to claim 1, wherein L is pyridine, dioxane, NH$_3$, THF, CO, an alkylphosphine, or an arylphosphine.

5. The metal complex according to claim 1, wherein the complex comprises a five-membered chelate ring.

6. The metal complex according to claim 1, wherein M is selected from the group consisting of aluminum (Al), gallium (Ga), indium (In), silicon (Si), germanium (Ge), tin (Sn), arsenic (As) and antimony (Sb), titanium (Ti), zirconium (Zr), hafnium (Hf), chromium (Cr), manganese (Mn), iron (Fe), cobalt (Co), nickel (Ni), copper (Cu) and zinc (Zn).

7. The metal complex according to claim 1, wherein M is selected from the group consisting of ruthenium (Ru), rhodium (Rh), palladium (Pd) and platinum (Pt).

8. The metal complex according to claim 1, wherein at least one of the ligands is an N-aminoamidinate ligand selected from the group consisting of N,N'-bis(dimethylamino)acetamidinate ("bdma"), N-mono(dimethylamino)acetamidinate ("dama"), mono(dimethylamino)acetamidinate ("mdma") and N,N'-bis(dimethylamino)formamidinate ("bdmf").

9. The metal complex according to claim 8, wherein at least one of the N-aminoamidinate ligands is an N,N'-bis(dimethylamino)acetamidinate ("bdma").

10. The metal complex according to claim 1, wherein the complex comprises a dimeric structure with bridging ligand functions X, Y or L.

11. A metal complex having at least one neutral N-aminoamidine ligand, wherein the metal complex is constructed according to general formula 2

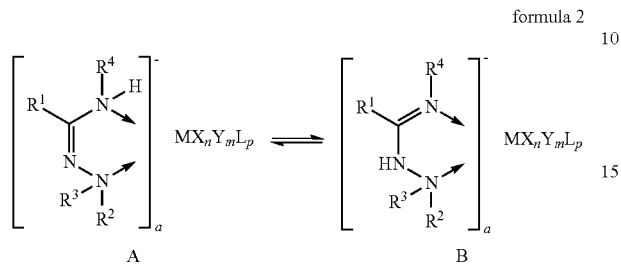

formula 2 wherein
M is a transition metal selected from group 1 or 11 of the Periodic Table of the Elements (PTE),
$R^1$ is hydrogen or a cyclic, linear or branched alkyl radical having up to 8 C atoms, or a substituted or unsubstituted aryl radical having up to 20 C atoms,
$R^2$ and $R^3$ independently of one another are hydrogen, $CH_3$ or $C_2H_5$,
$R^4$ is hydrogen, $CH_3$, $NH_2$, $N(CH_3)_2$ or $N(C_2H_5)_2$,
X is a monoanionic coligand selected from the group consisting of the hydride anion ($H^-$), the group of halides, the group of cyclic, linear or branched alkylide radicals with up to 8 C atoms, the group of substituted or unsubstituted arylide and heteroarylide radicals with up to 10 C atoms, the group of alkoxylato ligands, the group of alkylthiolato or alkylselenato ligands, and the group of secondary amido ligands,
Y is a dianionic co-ligand selected from the group consisting of the oxo group $[O]^{2-}$, and the imido group $[NR^5]^{2-}$, wherein $R^5$ is a cyclic, branched or linear alkyl radical with up to 8 C atoms or is a substituted or unsubstituted aryl radical with up to 20 C atoms,
L is a neutral 2-electron donor ligand, wherein the neutral N-aminoamidine ligand is N, N'-bis(dimethylamino)acetamidine ("H-bdma"),
a is an integer between 1 and 4, and
n, m and p each independently of one another are 0, 1, 2, 3 or 4.

12. A metal complex having N-aminoamidinate ligands in accordance with formula 4,

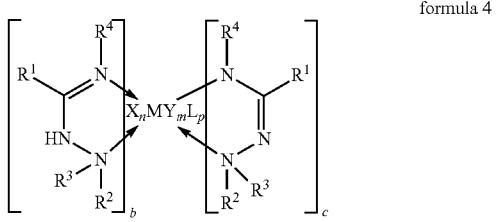

formula 4 wherein the monoanionic N-aminoamidinate ligands of index c and the neutral N-aminoamidino ligands of index b are combined in one complex and on one coordination centre,
and wherein the indices b and c independently of one another represent the integers 1, 2 or 3 and wherein
M is a metal selected from groups 1 to 15 of the Periodic Table of the Elements (PTE),
X is a monoanionic co-ligand selected from the group consisting of the hydride anion ($H^-$), the group of the halides, the group of the cyclic, linear or branched alkylide radicals having up to 8 C atoms, the group of substituted or unsubstituted arylide and heteroarylide radicals having up to 10 C atoms, the group of alkoxylato ligands, from the group of alkylthiolato or alkylselenato ligands, and the group of secondary amido ligands,
Y is a dianionic coligand selected from the group consisting of the oxo group $[O]^{2-}$, and the imido group $[NR^5]^{2-}$, where $R^5$ is a cyclic, branched or linear alkyl radical having up to 8 C atoms or is a substituted or unsubstituted aryl radical having up to 20 C atoms,
L is a neutral 2-electron donor ligand, and
n, m, and p each independently of one another are 0, 1, 2, 3 or 4.

13. A process for preparing the metal complex according to claim 1, comprising reacting a suitable metal starting compound with a neutral N-aminoamidine ligand in an organic solvent in an alkane or amine elimination.

14. A process for preparing the metal complex according to claim 1, comprising using a base to deprotonate the neutral N-aminoamidine ligand and subsequently reacting a suitable metal starting compound with the neutral N-aminoamidine ligand in an organic solvent in a salt elimination reaction.

15. The process according to claim 13, wherein the organic solvent comprises an aliphatic hydrocarbon, an aromatic solvent, a chlorinated solvent, an ethereal solvent or an alcohol.

16. The process according to claim 14, wherein the organic base is "Bu-lithium, lithium hexamethyldisilazide (LiHMDS) or potassium hexamethyldisilazide (KHMDS).

17. A metal complex having at least one N-aminoamidinate ligand, wherein the metal complex is constructed according to the general formula 1

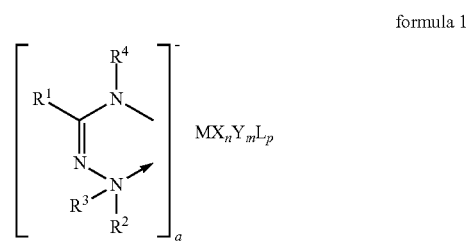

formula 1 wherein
M is a metal selected from groups 1 to 15 of the Periodic Table of the Elements (PTE),
$R^1$ is hydrogen or a cyclic, linear or branched alkyl radical having up to 8 C atoms, or a substituted or unsubstituted aryl radical having up to 20 C atoms,
$R^2$ and $R^3$ independently of one another are hydrogen, $CH_3$ or $C_2H_5$,
$R^4$ is hydrogen or a cyclic, linear or branched alkyl radical having up to 8 C atoms, $NH_2$, $N(CH_3)_2$ or $N(C_2H_5)_2$,
X is a monoanionic co-ligand selected from the group consisting of the hydride anion ($H^-$), the group of the halides, the group of the cyclic, linear or branched alkylide radicals having up to 8 C atoms, the group of substituted or unsubstituted arylide and heteroarylide radicals having up to 10 C atoms, the group of alkoxylato ligands, the group of alkylthiolato or alkylselenato ligands, and the group of secondary amido ligands, Y is a dianionic coligand selected from the group consisting of the oxo group $[O]^{2-}$ and the imido group $[NR^5]^{2-}$, where $R^5$ is a cyclic, branched or linear alkyl radical having up to 8 C atoms or is a substituted or unsubstituted aryl radical having up to 20 C atoms, L is a neutral 2-electron donor ligand, wherein if M is scandium, L is not a pentamethylcyclopentadiene (Cp*) ligand, a is an integer between 1 and 4, and n, m, and p each independently of one another are 0, 1, 2, 3 or 4.

18. The metal complex according to claim 17, wherein $R^4$ is an isopropyl radical.

19. The metal complex according to claim 17, wherein at least one of the N-aminoamidinate ligands is an N-dimethylamino-N'-isopropyl-acetamidinate ("dapa") ligand.

* * * * *